US011065126B2

(12) United States Patent
Newman et al.

(10) Patent No.: US 11,065,126 B2
(45) Date of Patent: Jul. 20, 2021

(54) INTERBODY IMPLANTS AND OPTIMIZATION FEATURES THEREOF

(71) Applicant: Stryker European Operations Holdings, LLC, Wilmington, DE (US)

(72) Inventors: Collin Newman, Wayne, NJ (US); Christian Karl Schultz, Hoboken, NJ (US); Steven Willis, Mahwah, NJ (US); Amir Ali Sharifi-Mehr, Bloomingdale, NJ (US); Oliver Buchert, Franklin Lakes, NJ (US); Christopher P. Bell, New York, NY (US); Andrew Edward Ehlers, Monroe, NY (US); Anna Reza, Montclair, NJ (US); Marc Gilles Long, Denville, NJ (US); Joseph Henry Robinson, Ridgewood, NJ (US)

(73) Assignee: Stryker European Operations Holdings LLC, Kalamazoo, MI (US)

(*) Notice: Subject to any disclaimer, the term of this patent is extended or adjusted under 35 U.S.C. 154(b) by 166 days.

(21) Appl. No.: 16/535,524

(22) Filed: Aug. 8, 2019

(65) Prior Publication Data
US 2020/0046512 A1   Feb. 13, 2020

Related U.S. Application Data

(60) Provisional application No. 62/716,448, filed on Aug. 9, 2018.

(51) Int. Cl.
*A61F 2/44* (2006.01)
*A61F 2/46* (2006.01)
*A61F 2/28* (2006.01)

(52) U.S. Cl.
CPC ............ *A61F 2/442* (2013.01); *A61F 2/4455* (2013.01); *A61F 2/4611* (2013.01); *A61F 2/2846* (2013.01);
(Continued)

(58) Field of Classification Search
CPC .......... A61F 2/44; A61F 2/442; A61F 2/4455; A61F 2/446; A61F 2/4465; A61F 2/447;
(Continued)

(56) References Cited

U.S. PATENT DOCUMENTS

| 896,710 A | 8/1908 | Ross |
| 3,852,045 A | 12/1974 | Wheeler et al. |

(Continued)

FOREIGN PATENT DOCUMENTS

| CN | 102293693 B | 6/2013 |
| EP | 0505634 A1 | 9/1992 |

(Continued)

OTHER PUBLICATIONS

European Search Report for Application No. 19190934.0 dated Jan. 8, 2020, 5 pages.

(Continued)

*Primary Examiner* — Eric S Gibson
(74) *Attorney, Agent, or Firm* — Lerner, David, Littenberg, Krumholz & Mentlik, LLP

(57) ABSTRACT

A spinal interbody device (IBD) includes a solid wall that at least partially defines a boundary of the IBD and a porous body connected to the solid wall. The porous body includes a plurality of sections that form at least a portion of both a superior and inferior bone interface side of the IBD. Each section of the porous body has a different porosity than an adjacent section such that the porosities increase toward a center of the IBD.

20 Claims, 19 Drawing Sheets

(52) U.S. Cl.
CPC .......... *A61F 2002/2835* (2013.01); *A61F 2002/4629* (2013.01); *A61F 2250/0018* (2013.01); *A61F 2310/00023* (2013.01)

(58) Field of Classification Search
CPC .... A61F 2002/30011; A61F 2002/3093; A61F 2002/4495
See application file for complete search history.

(56) References Cited

U.S. PATENT DOCUMENTS

| | | | |
|---|---|---|---|
| 3,855,638 | A | 12/1974 | Pilliar |
| 4,612,160 | A | 9/1986 | Donlevy et al. |
| 4,863,538 | A | 9/1989 | Deckard |
| 4,944,817 | A | 7/1990 | Bourell et al. |
| 5,017,753 | A | 5/1991 | Deckard |
| 5,071,437 | A | 12/1991 | Steffee |
| 5,076,869 | A | 12/1991 | Bourell et al. |
| 5,263,986 | A | 11/1993 | Noiles et al. |
| 5,370,692 | A | 12/1994 | Fink et al. |
| 5,458,643 | A | 10/1995 | Oka et al. |
| 5,504,300 | A | 4/1996 | Devanathan et al. |
| 5,507,815 | A | 4/1996 | Wagner et al. |
| 5,672,284 | A | 9/1997 | Devanathan et al. |
| 5,734,959 | A | 3/1998 | Krebs et al. |
| 5,768,134 | A | 6/1998 | Swaelens et al. |
| 5,961,554 | A | 10/1999 | Janson et al. |
| 6,149,688 | A | 11/2000 | Brosnahan et al. |
| 6,471,725 | B1 | 10/2002 | Ralph et al. |
| 6,485,521 | B1 | 11/2002 | Say et al. |
| 6,533,818 | B1 | 3/2003 | Weber |
| 6,569,201 | B2 | 5/2003 | Moumene et al. |
| 6,572,654 | B1 | 6/2003 | Santilli |
| 6,623,525 | B2 | 9/2003 | Ralph et al. |
| 6,673,075 | B2 | 1/2004 | Santilli |
| 6,740,186 | B2 | 5/2004 | Hawkins et al. |
| 6,790,233 | B2 | 9/2004 | Brodke et al. |
| 6,863,689 | B2 | 3/2005 | Ralph et al. |
| 6,911,249 | B2 | 6/2005 | Wagner et al. |
| 7,135,042 | B2 | 11/2006 | Stoll |
| 7,238,203 | B2 | 7/2007 | Bagga et al. |
| 7,241,313 | B2 | 7/2007 | Unwin et al. |
| 7,497,876 | B2 | 3/2009 | Tuke et al. |
| 7,635,447 | B2 | 12/2009 | Hamman et al. |
| 7,662,186 | B2 | 2/2010 | Bagga et al. |
| 7,922,765 | B2 | 4/2011 | Reiley |
| 8,147,861 | B2 | 4/2012 | Jones et al. |
| 8,262,737 | B2 | 9/2012 | Bagga et al. |
| 8,266,780 | B2 | 9/2012 | Bollinger et al. |
| 8,268,100 | B2 | 9/2012 | O'Neill et al. |
| 8,303,879 | B2 | 11/2012 | Bertele et al. |
| 8,361,153 | B2 | 1/2013 | Ralph et al. |
| 8,403,991 | B2 | 3/2013 | Ullrich, Jr. et al. |
| 8,414,654 | B1 | 4/2013 | Ganey |
| 8,425,604 | B2 | 4/2013 | Trieu |
| 8,435,302 | B2 | 5/2013 | Ulrich, Jr. et al. |
| 8,480,749 | B2 | 7/2013 | Ullrich, Jr. et al. |
| 8,530,560 | B2 | 9/2013 | Kerr et al. |
| 8,532,806 | B1 | 9/2013 | Masson |
| 8,545,568 | B2 | 10/2013 | Ulrich, Jr. et al. |
| 8,545,572 | B2 | 10/2013 | Olson |
| 8,551,173 | B2 | 10/2013 | Lechmann et al. |
| 8,551,176 | B2 | 10/2013 | Ullrich, Jr. et al. |
| 8,556,981 | B2 | 10/2013 | Jones et al. |
| 8,562,684 | B2 | 10/2013 | Ullrich, Jr. et al. |
| 8,585,767 | B2 | 11/2013 | Ullrich, Jr. et al. |
| 8,617,248 | B2 | 12/2013 | Ullrich, Jr. et al. |
| 8,632,604 | B2 | 1/2014 | Brooks |
| 8,735,773 | B2 | 5/2014 | Lang |
| 8,979,934 | B2 | 3/2015 | Kirschman |
| 8,992,619 | B2 | 3/2015 | Patterson et al. |
| 9,243,278 | B2 | 1/2016 | Morgan et al. |
| 9,415,137 | B2 | 8/2016 | Meridew et al. |
| 9,456,901 | B2 | 10/2016 | Jones et al. |
| 9,700,431 | B2* | 7/2017 | Nebosky ............... A61F 2/3094 |
| 9,724,203 | B2 | 8/2017 | Nebosky et al. |
| 9,848,995 | B2 | 12/2017 | Ullrich, Jr. et al. |
| 10,016,811 | B2 | 7/2018 | Neal |
| 10,512,545 | B2* | 12/2019 | Arnone ............... A61F 2/30907 |
| 10,792,129 | B2* | 10/2020 | Spivack ............... A61L 27/60 |
| 10,835,388 | B2* | 11/2020 | Milz ............... A61F 2/4455 |
| 2003/0055505 | A1 | 3/2003 | Sicotte et al. |
| 2004/0133279 | A1 | 7/2004 | Krueger et al. |
| 2005/0123672 | A1 | 6/2005 | Justin et al. |
| 2005/0177238 | A1 | 8/2005 | Khandkar et al. |
| 2005/0203630 | A1 | 9/2005 | Pope et al. |
| 2007/0218098 | A1 | 9/2007 | Reif et al. |
| 2008/0161927 | A1 | 7/2008 | Savage et al. |
| 2008/0183292 | A1 | 7/2008 | Trieu |
| 2008/0306595 | A1 | 12/2008 | McLeod et al. |
| 2009/0093885 | A1 | 4/2009 | Levieux et al. |
| 2009/0222098 | A1* | 9/2009 | Trieu ............... A61L 27/50 623/17.16 |
| 2010/0042218 | A1 | 2/2010 | Nebosky et al. |
| 2010/0076559 | A1 | 3/2010 | Bagga et al. |
| 2010/0094426 | A1 | 4/2010 | Grohowski, Jr. et al. |
| 2010/0137990 | A1 | 6/2010 | Apatsidis et al. |
| 2010/0256773 | A1 | 10/2010 | Thijs et al. |
| 2010/0262244 | A1 | 10/2010 | Savage-Erickson et al. |
| 2011/0012280 | A1 | 1/2011 | Deslauriers et al. |
| 2011/0015743 | A1* | 1/2011 | Deslauriers ........... A61F 2/4455 623/17.16 |
| 2011/0071635 | A1* | 3/2011 | Zhang ............... B32B 27/288 623/17.11 |
| 2011/0282392 | A1 | 11/2011 | Murphy et al. |
| 2011/0285454 | A1 | 11/2011 | Bayramoglu |
| 2011/0313538 | A1* | 12/2011 | Oh ............... A61L 27/56 623/23.61 |
| 2012/0150299 | A1* | 6/2012 | Ergun ............... B29C 48/54 623/17.11 |
| 2012/0265306 | A1 | 10/2012 | Trieu |
| 2012/0303127 | A1 | 11/2012 | Ullrich, Jr. et al. |
| 2012/0312778 | A1 | 12/2012 | Ullrich, Jr. et al. |
| 2012/0312779 | A1 | 12/2012 | Patterson et al. |
| 2012/0330420 | A1 | 12/2012 | Brodke et al. |
| 2013/0116793 | A1* | 5/2013 | Kloss ............... A61F 2/442 623/17.16 |
| 2013/0274886 | A1 | 10/2013 | Matsumoto et al. |
| 2013/0282122 | A1 | 10/2013 | Ullrich, Jr. et al. |
| 2013/0325129 | A1* | 12/2013 | Huang ............... A61F 2/2803 623/17.16 |
| 2014/0107786 | A1* | 4/2014 | Geisler ............... A61F 2/4455 623/17.16 |
| 2014/0114415 | A1 | 4/2014 | Tyber |
| 2014/0121776 | A1 | 5/2014 | Hunt |
| 2014/0207237 | A1 | 7/2014 | Kerr et al. |
| 2014/0264995 | A1* | 9/2014 | Lakshminarayanan ...... A61F 2/442 264/54 |
| 2014/0277461 | A1* | 9/2014 | Nebosky ............... A61F 2/442 623/17.11 |
| 2014/0277491 | A1* | 9/2014 | Fang ............... A61F 2/447 623/17.16 |
| 2015/0018956 | A1 | 1/2015 | Steinmann et al. |
| 2015/0045903 | A1* | 2/2015 | Neal ............... B23K 26/354 623/21.18 |
| 2015/0134063 | A1 | 5/2015 | Steinmann et al. |
| 2016/0157908 | A1 | 6/2016 | Cawley et al. |
| 2016/0270920 | A1* | 9/2016 | Dawson ............... A61F 2/4601 |
| 2016/0346088 | A1 | 12/2016 | Meridew et al. |
| 2017/0020685 | A1* | 1/2017 | Geisler ............... A61F 2/442 |
| 2017/0056190 | A1 | 3/2017 | Guilford et al. |
| 2017/0095337 | A1 | 4/2017 | Pasini et al. |
| 2017/0156878 | A1* | 6/2017 | Tsai ............... A61B 17/86 |
| 2017/0165085 | A1 | 6/2017 | Lechmann et al. |
| 2020/0046512 | A1* | 2/2020 | Newman ............... A61F 2/442 |

FOREIGN PATENT DOCUMENTS

| | | | |
|---|---|---|---|
| EP | 1961433 | A1 | 8/2008 |
| WO | 9920208 | A1 | 4/1999 |

(56) References Cited

FOREIGN PATENT DOCUMENTS

| WO | 2006121795 A2 | 11/2006 |
| WO | 2015017324 A1 | 2/2015 |
| WO | 2017106780 A1 | 6/2017 |

OTHER PUBLICATIONS

Milz et al, U.S. Appl. No. 62/560,910, filed Sep. 20, 2017, Titled "Spinal Implants".

* cited by examiner

INTERBODY IMPLANTS AND OPTIMIZATION FEATURES THEREOF

CROSS-REFERENCE TO RELATED APPLICATIONS

This application claims the benefit of the filing date of U.S. Provisional Application No. 62/716,448, filed Aug. 9, 2018, the disclosure of which is hereby incorporated by reference.

BACKGROUND OF THE INVENTION

Orthopedic implants are commonly connected to bone in order to provide support while a fracture heals, to reconstruct bone that is missing due to disease or injury, to replace a damaged or diseased joint, or to fuse bones together, such as across a joint. Several means of fixation have emerged over the years that help provide a secure connection between the implant and bone. Such means include bone screws, bone cement, ultrasonic pins, bone grafts, porous structures, and the like. Porous structures and bone grafts are commonly employed to encourage bone to grow into the implant as though the implant were an extension of the bone. However, fusion between implant and bone does not always occur as desired, due to stress shielding or other reasons. Moreover, porous structures are generally more difficult to visualize via radiographic imagery than solid, nonporous structures.

When bone grafts are deployed in conjunction with orthopedic implants, they are typically packed into a space provided by an opening of the implant. When the implant is implanted, the bone graft is brought into contact with the bone to encourage bone growth into the implant's opening. Spinal implants, such as fusion cages, commonly have one or more graft windows for this purpose. However, these graft windows generally occupy a significant portion of the implant's footprint so that usually all that remains is an outer shell, ring-like structure, and the like with a negative space in the middle of it. Since bone graft within a fusion cage's graft window is not initially load bearing, loads are concentrated on a smaller area of the cage than if the negative space created by the graft window were also load bearing. Thus, fusion cages may be susceptible to subsidence or fracture. However, the stiffness of such implants can result in stress shielding, which may limit bone ingrowth. In addition, fusion cages with graft windows tend to have little space for porous structures, which may limit the amount of bone that can grow directly into the implant.

Thus, despite the improvements that have been made to orthopedic implants, further improvements are desirable.

BRIEF SUMMARY OF THE INVENTION

The present disclosure describes optimization features that can be employed in orthopedic implants, such as, for example, a spinal interbody device ("IBD"), to help promote fixation of such implants to bone, help visualize the implant via radiographic imagery, and provide strength to the implant so that such implant is durable throughout its lifetime while also providing for strain induced cellular response, limiting stress shielding, migration of cells, and flow of nutrients. Such features include varying porosities, tissue through-channels, bioactive substance integration, porous structure cell strain optimization, and composite-like structures which include nonporous portions and porous portions formed into a unitary or monolithic device.

In one aspect of the present disclosure, a spinal interbody device (IBD) includes a solid wall at least partially defining a boundary of the IBD, and a porous body connected to the solid wall. The porous body includes a plurality of sections forming at least a portion of both a superior and inferior bone interface side of the IBD. Each section of the porous body has a different porosity than an adjacent section such that the porosities increase toward a center of the IBD.

Additionally, the plurality of sections may include first and second sections. The first section may form a ring about the second section. Also, at least the first section may be impregnated with a bioactive material so that particles of the bioactive material are disposed within pores of the porous first section. A pore size of the second section may be smaller than a particle size of the bioactive material such that the second section is substantially free from the bioactive material. Solid projections may also be embedded in the porous body and may extend from the superior and inferior bone interface sides of the IBD.

Also, the IBD may further include a plurality of elongate through-channels extending entirely through the porous body from the superior bone interface side to the inferior bone interface side of the IBD. Further, a plurality elongate struts may each partially define a perimeter of a respective one of the elongate through-channels.

Continuing with this aspect, the porous body may include a plurality of adjoined cells that collectively define a plurality of pores of the porous body. Each cell of the porous body may have a plurality of connected members. The members of each cell may have a different cross-sectional dimension based on their expected loads such that they each have a strain of between 1000 and 1800 micro strain when implanted in a disc space. The cells of the porous body may each have a geometric shape selected from the group consisting of a diamond cubic, single cubic, body-centered cubic, face centered cubic, tetrahedron, dodecahedron, or octahedron. Each section of the porous body may include cells of a different geometric shape than an adjacent section. The porous body may completely fill a space confined by the solid wall. The solid wall may also include bone engaging projections extending from superior and inferior sides thereof.

In another aspect of the present disclosure, a spinal IBD includes a solid wall, and a porous body positioned within a boundary defined by the solid wall. The porous body may have a plurality of sections such that a first section of the plurality of sections forms an outer bone contacting layer of the porous body, and a second section of the plurality of sections forms an inner layer of the porous body so that when the IBD is implanted within a disc space defined partially by a vertebra, the first section is positioned closer to the vertebra than the second section. The first section may have a first porosity that differs from a porosity of the second section.

Additionally, the first section may have a smaller porosity than the second section. Alternatively, the first section may have a greater porosity than the second section. Also, at least the first section may be impregnated with a bioactive material so that particles of the bioactive material are disposed within pores of the porous first section. A pore size of the second section may be smaller than a particle size of the bioactive material such that the second section is substantially free from the bioactive material. Also, solid projections may be embedded in the first section of the porous body and may extend therefrom.

Also, the IBD may further include a plurality of elongate through-channels extending entirely through the porous body from a superior side to an inferior side of the IBD. The IBD may also include a plurality of elongate struts each partially defining a perimeter of a respective one of the elongate through-channels.

Continuing with this aspect, the porous body may include a plurality of adjoined cells that collectively define a plurality of pores of the porous body. Each cell of the porous body may have a plurality of connected members. The members of each cell may have a different cross-sectional dimension based on their expected loads such that they each have a strain of between 1000 and 1800 micro strain when implanted in a disc space. The cells of the porous body may each have a geometric shape selected from the group consisting of a diamond cubic, single cubic, body-centered cubic, face centered cubic, tetrahedron, dodecahedron, or octahedron. Further, each section of the porous body includes cells of a different geometric shape than an adjacent section. The porous body may completely fill a space confined by the solid wall. The solid wall includes bone engaging projections extending from superior and inferior sides thereof.

In a further aspect of the present disclosure, a spinal IBD includes a porous body having a leading end, a trailing end, and opposing bone contacting sides situated therebetween. The IBD also includes a solid reinforcing structure embedded in the porous body such that porous body completely surrounds the reinforcing structure. The reinforcing structure has a plurality of intersecting members forming openings therebetween.

Additionally, the plurality of intersecting members may include a first member extending in a first direction and a second member extending in a second direction. The first and second directions may be transverse to each other and may extend in a plane situated between the opposing bone contacting sides of the porous body 30. The reinforcing structure may be a rectangular grid and the plurality of intersecting members may perpendicularly intersect. The reinforcing structure may be one of a plurality of reinforcing structures arranged in layers within porous body. The porous body may extend through the openings defined by the reinforcing structure. The porous body may be comprised of porous sections each having a different porosity. The porous body may be impregnated with a bioactive material.

Also, the IBD may further include through-channels extending entirely through the porous body and opposing bone engaging sides thereof. The through-channels may extend through a respective opening in the reinforcing structure. Further, the IBD may include elongate struts extending along each of the through-channels, which may partially define a perimeter thereof.

In an even further aspect of the present disclosure, an IBD includes a porous body defined by a plurality of adjoining cells that collectively define a plurality of pores, and a bioactive material dispersed within the porous body such that particles of the bioactive material reside at least some of the pores of the porous structure.

Additionally, the bioactive material may be one of a silicate bioglass, borate bioglass, borosilicate bioglass and sol-gel derived bone graft. The porous body may also include a plurality of porous sections with differing porosities such that one or more of the porous sections have a pore size larger than a particle size of the bioactive material and one or more of the porous sections may have a pore size smaller than a particle size of the bioactive material. The IBD may even have a solid outer wall surrounding the porous body.

Continuing with this aspect, the IBD may include a graft window extending through the porous body from a superior side to an inferior side thereof. The graft window may be defined by the porous body such that the graft window directly communicates with some of the pores of the porous body. The bioactive material may be disposed in the graft window. The graft window, alternatively, may be substantially free of the bioactive material.

Also, the IBD may include elongate through-channels extending entirely through the porous structure from the superior side to the inferior side of the porous body. The IBD may also include struts extending along each of the through-channels and partially defining a perimeter thereof. Further, solid bone engaging projections may be embedded in the porous body at the superior and inferior sides thereof.

In yet a further aspect of the present disclosure, an IBD includes a solid wall defining at least a portion of a perimeter of the IBD. The IBD also includes a porous body connected to the solid wall and defined by a plurality of adjoined cells and pores situated between the cells. Further, the IBD includes a plurality of elongate through-channels extending through the porous body from first bone contacting side to a second bone contacting side thereof. The through-channels each include a longitudinal axis and are defined by the porous body such that the through-channels directly communicate with some of the pores of the porous body. Even further, the IBD includes a plurality of elongate struts that extend along respective ones of the through-channels from the first bone contacting side to the second bone contacting side.

In still a further aspect of the present disclosure, includes a solid portion, and a porous portion connected to the solid portion. The porous portion has a plurality of sections comprising a bone contacting face of the implant such that each section of the porous portion contacts bone when implanted. The plurality of sections each have a different porosity based on respective bone densities of a bone into which the implant is to be implanted so that when the implant is implanted in the bone, the porous sections have a higher porosity than the other porous sections that are positioned adjacent to relatively low density bone and so that the porous sections have a lower porosity than other porous sections that are positioned adjacent to relatively high density bone.

In yet another aspect of the present disclosure, an IBD includes a solid portion, and a porous portion connected to the solid portion. The porous portion has a plurality of sections each having a differing porosity than an adjacent section. The sections include a first section that forms an outer bone contacting layer of the porous portion, and a second section that forms an inner layer of the porous portion disposed adjacent the first section. The first section has a first porosity greater than a second porosity of the second section.

In a further aspect of the present disclosure, a method of manufacturing a porous material for an orthopedic implant includes selecting a cell geometry comprised of a plurality of interconnected struts for a lattice structure of a porous material; determining theoretical loads applied to each struts of the cell during use; adjusting one of the cross-sectional dimension and length of each strut of the cell so that during use the strain within each strut is between 1000 and 1800 micro strain; and forming the porous material having the cell using an additive manufacturing process.

In an even further aspect of the present disclosure, a method of manufacturing an orthopedic implant includes forming an implant layer by layer via an additive manufacturing process such that the implant includes a solid support portion and a porous portion that forms a portion of the implants exterior for interfacing with a bone; inserting the implant into a mold; and injecting a bioactive material into the mold such that the bioactive material is dispersed into a portion of the implant.

In yet a further aspect of the present disclosure, a method of manufacturing an IBD includes forming the IBD layer by layer via an additive manufacturing process such that the IBD includes a solid outer wall and a porous body that forms a portion of a bone contacting side of the IBD; inserting the implant into a mold; and injecting a bioactive material into the mold such that the bioactive material is dispersed into a portion of the implant.

Also, the method may include plugging a graft window in the IBD prior to the inserting step, and removing the plug after the injecting step so that the graft window remains free of the bioactive material. The method may also include removing a layer of the bioactive material from the porous body so as to expose an outer surface of the porous body. The injecting step may include injecting the bioactive material in a sol-gel state. The method may also include demolding the IBD after the bioactive material solidifies.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. The term "inferior" means toward the feet and the term "superior" means toward the head. Also, as used herein, the terms "about," "generally" and "substantially" are intended to mean that slight deviations from absolute are included within the scope of the term so modified. To aid the Patent Office and any readers of any patent issued on this application in interpreting the claims appended hereto, Applicant notes that it does not intend any of the appended claims or claim elements to invoke 35 U.S.C. 112(f) unless the words "means for" or "step for" are explicitly used in the particular claim.

Bones are highly adaptive and change in response to external stimuli, such as stress. Bones typically include dense cortical bone and spongy cancellous bone. Cancellous bone has a porous structure that includes blood vessels, bone marrow, and stem cells which repair damaged or broken bone. Orthopedic implants often have porous structures which are intended to contact cancellous bone and encourage bone tissue growth therein.

Figure 1A:
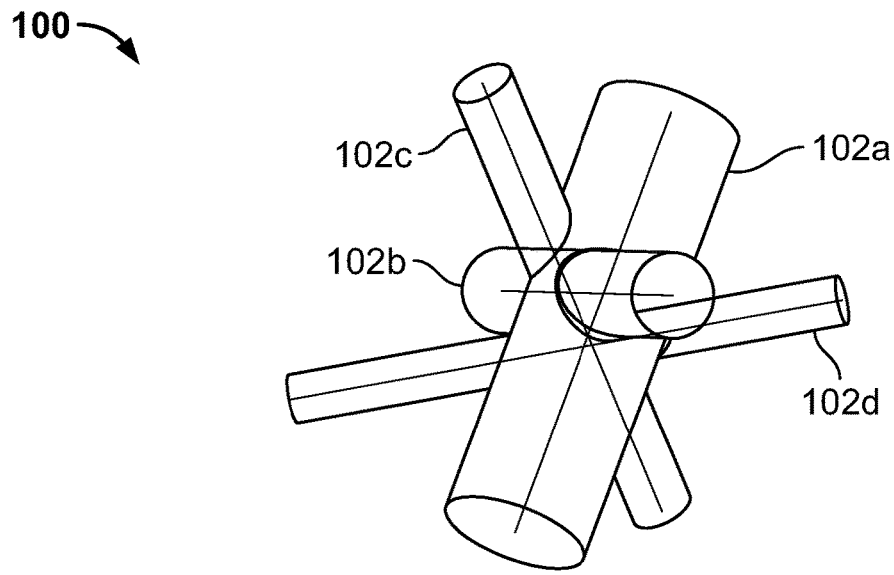
FIG. 1A is a variable cell of a porous material according to an embodiment of the present disclosure.
Figure 1B:
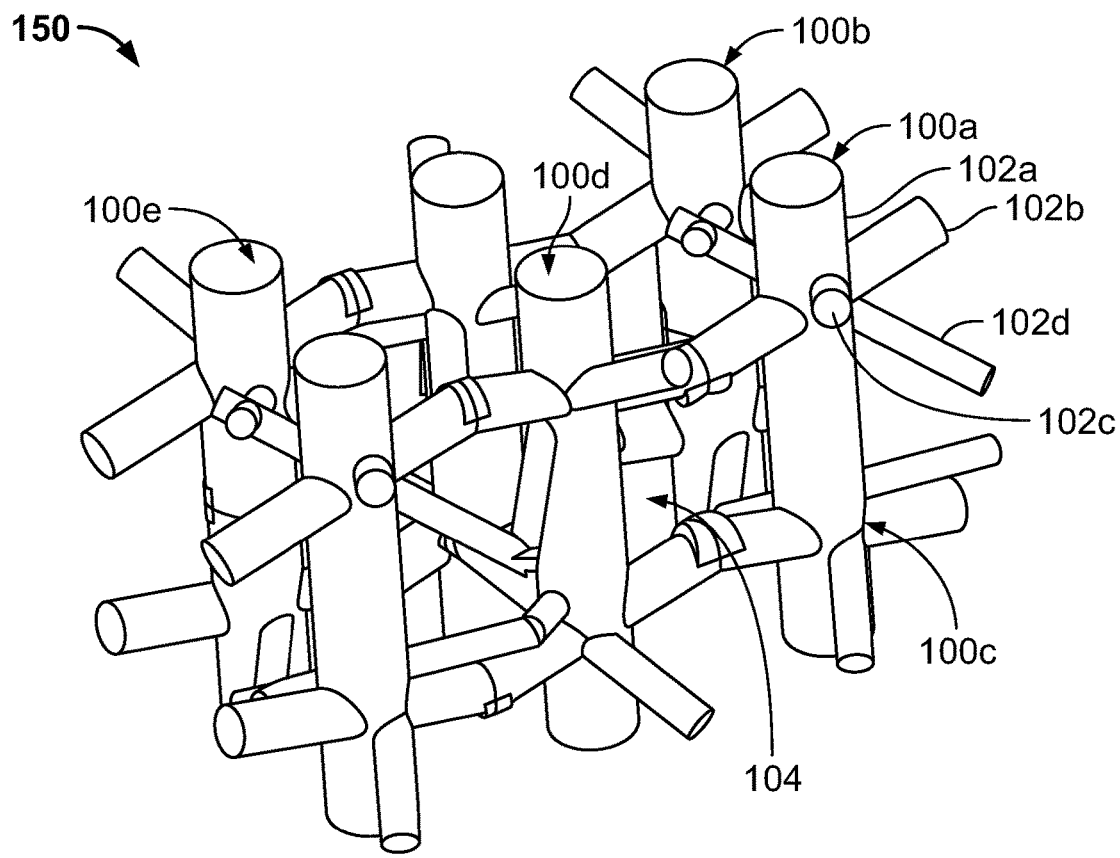
FIG. 1B is a lattice structure comprised of the variable cell of FIG. 1A.

FIGS. 1A and 1B depict a porous structure for use in an orthopedic implant according to an embodiment of the disclosure. The porous structure is comprised of adjoined cells which together form a porous material volume. FIG. 1A depicts a cell 100 of the porous structure. Such cell 100 includes a plurality of intersecting members or struts 102*a*-

*d.* As shown in FIG. 1B, a plurality interconnected cells 100 form a lattice structure. In this regard, struts 102*a-d* of cell 100*a* are connected to struts of adjacent cells 100*b-d* so as to form the lattice/porous structure of cells 100. The struts 102 of the adjoining cells 100*a-d* define pores or empty spaces 104 of the porous structure. The totality of these empty spaces 104 can be expressed as the porous structure's porosity. Porosity is generally a measure of a structure's empty space relative to the total space occupied by the structure (i.e., the volume occupied by both the struts 102 and empty space therebetween). More specifically porosity is characterized by the equation $\Psi=V_V/V_T$ where $\Psi$ is the porosity, $V_V$ is the volume of empty space or void-space, and $V_T$ is the total volume including the volume of materials defining the void-space and the void-space itself.

Studies suggest that strain is important for stimulating bone growth via a strain induced cellular response. In this regard, the strain exhibited by a porous material of a prosthetic implant under normal operating loads can encourage bone growth into the porous structure. Thus, when bone cells are in contact with a porous material, strain is an important factor in stimulating new bone growth. The inventors have found that the cells of a porous structure can be optimized by adjusting one or more geometric parameters of the cell so that the struts or members that comprise the cell exhibit a strain under operating loads that is within a target range of about 1000 to 1800 micro strain, which has been determined to be optimal for promoting bone growth without sacrificing needed strength. These parameters include the length and cross-sectional area of each individual strut that make up a cell. Indeed, struts can be tapered so that the cross-sectional dimension of a particular strut varies along its length. In addition, the overall shape or geometry of the cell, the total number of struts in a particular cell, the cross-sectional shape of the struts, the angulation of intersecting struts, the location of connection between two or more struts (i.e., the location along the length of any given strut the intersection of another strut occurs), and the like can also be adjusted to achieve an operating strain within the desired range.

Cell 100 is illustrative of such strain optimization. More particularly, as best shown in FIG. 1A, the cross-sectional dimensions of cell 100 decrease in order from first strut 102*a* to fourth strut 102*d*. The differences of the cross-sectional dimensions can be used to achieve the desired strain in each strut 102*a-d* based on the expected loads imposed on each strut 102*a-d*. In this regard, first strut 102*a* has the largest cross-sectional dimension as it is oriented in a direction of the largest load. Thus, it is contemplated that in some embodiments, depending on the expected load, some struts 102 may have the same cross-sectional dimensions and same lengths. Also, as shown, second, third, and fourth struts 102*b-d* each intersect first strut 102*a* such that their respective axes are obliquely angled relative to each other. In porous structure 150, struts 102*a-d* of cell 100*a* are connected to similarly sized struts 102 of adjacent cells 100*b-d*. However, it should be understood that depending on the loads imposed on porous structure 150, like struts 102 can vary in size and length over porous structure 150 to ensure the resulting strain is within the target strain range. Thus, corresponding struts 102 of cell 100*e*, which is remote from cell 100*a*, may have different lengths and/or cross-sectional dimensions.

Also, the lengths of each strut 102*a-d* in cell 100 may be increased or decreased to achieve the desired porosity while the cross-sectional dimension thereof can be increased or decreased to ensure struts 102*a-d* stay within the desired strain range criteria. In the embodiment depicted in FIG. 1B, the porosity of the porous structure 150 may be about 10% to 90% with an average pore size of between 20-1000 microns. However, porous structure 150 preferably includes a pore size of between 100 and 700 microns with a mean pore size of 400 to 500 microns and a mean porosity of 55% to 65%.

As mentioned above, other parameters can be adjusted to optimize mechanical strain, such as the number of struts and their angles of intersection, Thus while the cell 100 discussed above has four intersecting struts 102*a-d*, it should be understood that the above principles can be applied to the struts of cell structures having more or less struts and having differing geometric orientations of such struts. Examples of such cells are described in U.S. Pat. No. 9,456,901 ("the '901 Patent") and U.S. Pat. No. 9,135,374, which are incorporated by reference herein in their entirety. In this regard, the struts of such disclosed cells may be varied in length and cross-sectional dimension to achieve the desired strain under normal operating conditions. Moreover, the cells and porous structures described above can be made through an additive manufacturing process as detailed in the '901 Patent and as described further below.

As indicated above, the length of struts 102 of each cell 100 within porous structure 150 may be increased or decreased to achieve the desired porosity. This allows the porosity of the porous structure to be varied throughout the porous material of an implant. Thus, a porous structure may have regions of high porosity where strut length of the porous structure's cells are longer than in regions of relatively low porosity. This also allows the porosity of the structure to gradually decrease/increase between regions of minimum and maximum porosities.

Pore size can also be controlled by varying cell geometry. This may provide a discontinuous porosity change where abrupt changes in porosity may be desired. Thus, a porous structure may have cells of the geometry of cell 100 and other cells of a different geometry. Some of the different cell geometries that can be combined with each other and cell of FIG. 1A to vary porosity and to optimize strain include diamond cubic, single cubic, body-centered cubic, face centered cubic, tetrahedron, dodecahedron, and octahedron, to name a few. Some of these cell geometries and methods of manufacturing the same are described in the heretofore referenced '901 Patent. Varying porosities are exemplified in several of the following implant embodiments, discussed below.

All of the geometric parameters mentioned herein, including others not specifically mentions, that effect strain can be further optimized to achieve strain targets using computer aided design and topology optimization tools. However, until now, such optimization tools have never allowed for a strain range between a non-zero minimum and non-zero maximum to dictate the geometry of a cell and lattice structure.

Figure 2A:
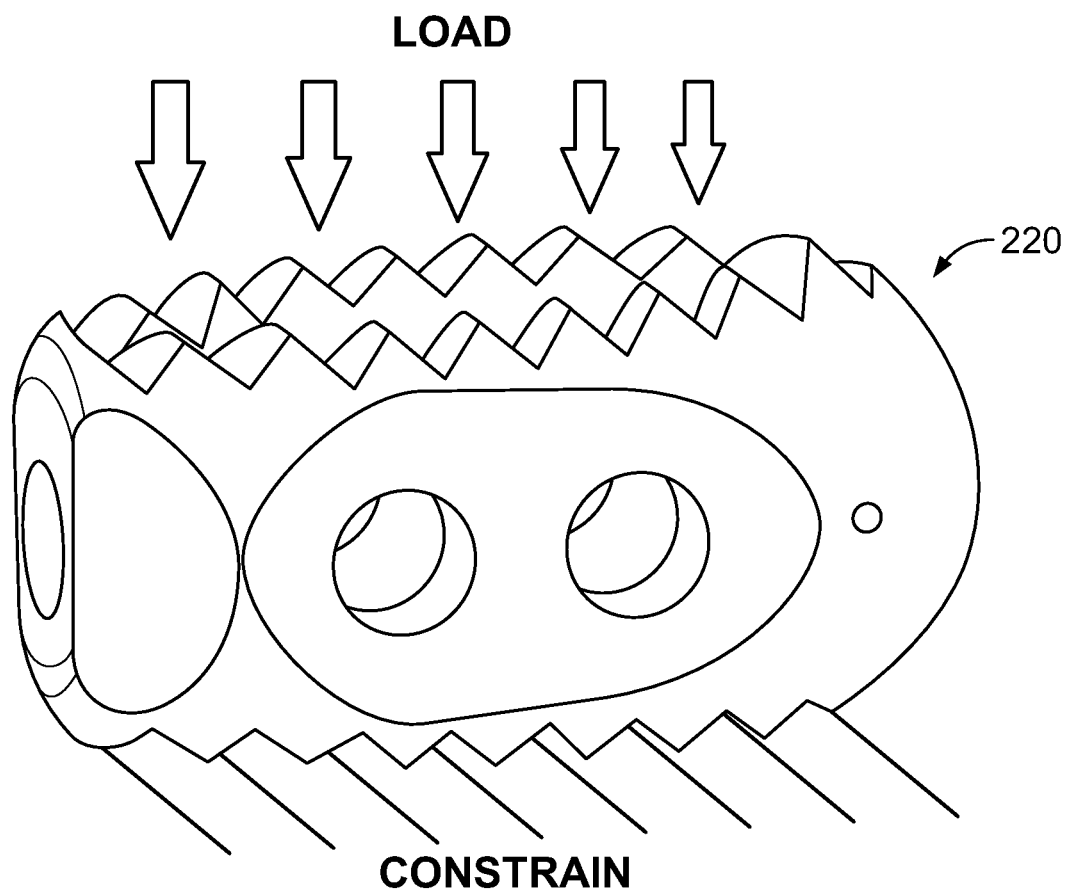
FIG. 2A illustrates an IBD, according to an embodiment of the disclosure, under a predetermined load.
Figure 2B:
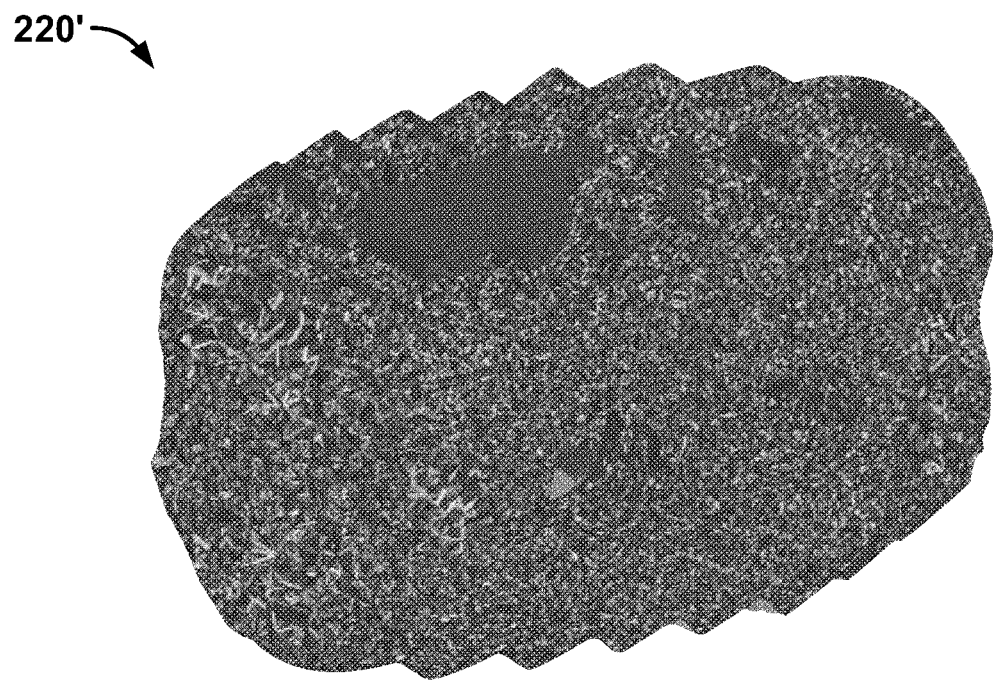
FIG. 2B illustrates a resulting porous topology of the IBD of FIG. 2D based on a structural analysis under the predetermined load.

A case study, depicted in FIGS. 2A and 2B, demonstrates strain optimization using structural analysis tools. In this regard, a sample IBD 220 was constrained at an inferior side thereof and fixed in all planes to replicate the constraint of such IBD in an intervertebral space. A sample load of 360 N was applied to a superior side of IBD 220 to replicate normal operating loads within the intervertebral space. The target strain range for the struts of the porous structure was set to be between 1000 and 1500 micro strains, and the target strut size was set to be between 0.4 mm and 0.8 mm. The resulting porous structure is depicted in FIG. 2B, which includes a variable size struts throughout the IBD 220, which each have a strain within the predetermined range under the sample load.

Figure 2C:
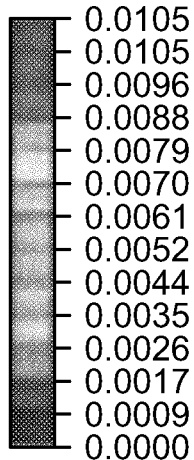
FIG. 2C is a strain map of a porous structure according to one embodiment of the present disclosure comprised of the cells of FIG. 1A.
Figure 2C:
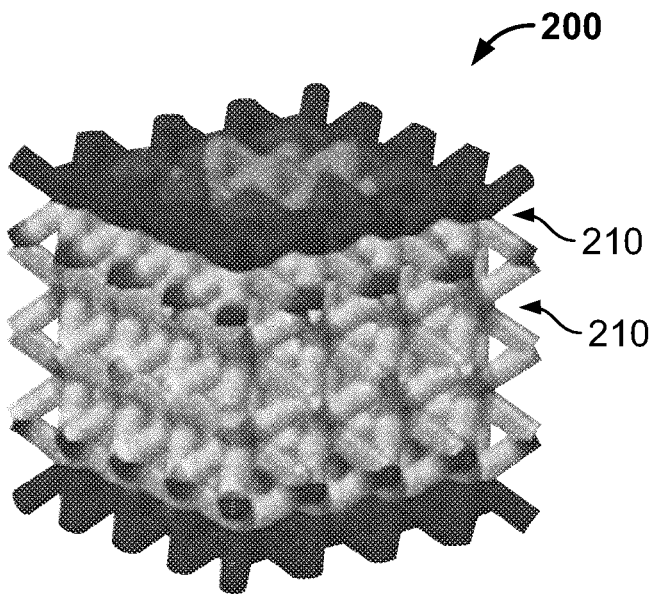
Figure 2D:
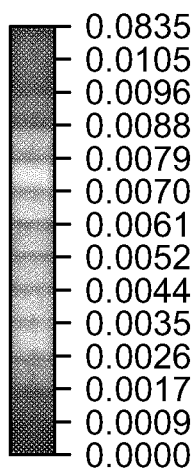
FIG. 2D is a strain map of a porous structure according to another embodiment of the present disclosure.
Figure 2D:
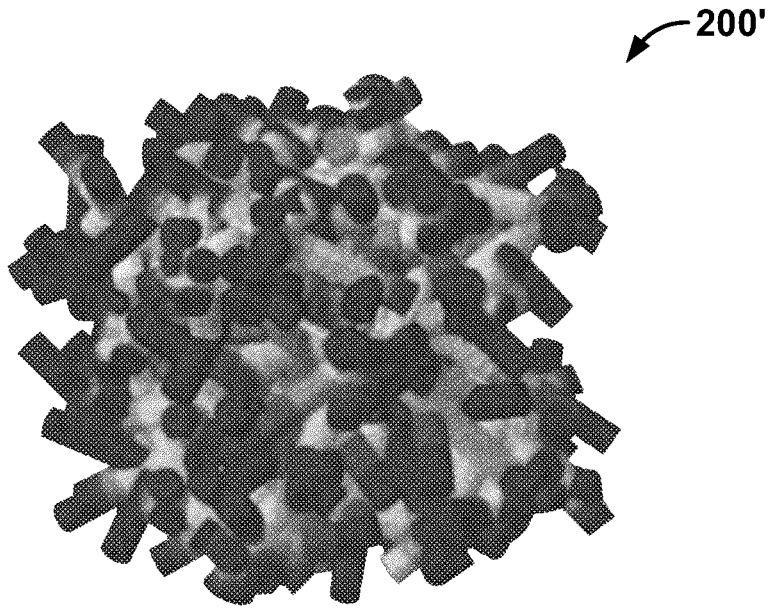

FIG. 2C depicts a strain map where a porous structure 200 is optimized to have a uniform strain within a target range throughout the entire volume, while FIG. 2D depicts a strain map in which a porous structure 200' is not optimized for strain. Such porous structure 200' has a non-uniform strain throughout the entire volume and has regions of very high and very low strain. Additionally, it should be pointed out that, while the porous structure 200' of FIG. 2D has a randomized pattern of cells, such randomization would not preclude strain optimization. Indeed, the struts of porous structure 200' can be adjusted in length and cross-sectional dimension so that even structure 200' could exhibit a uniform strain throughout.

Thus, as discussed above, an IBD, or some other prosthetic implant with a porous structure, may manufactured by designating a bone growth region or regions of the implant. A target/predetermined strain range between a minimum non-zero strain and a maximum non-zero strain determined to be conducive to a strain induced cellular response may then be selected. The geometry, such as length and cross-sectional dimension, of the struts of each cell in the designated bone growth region of the implant's porous structure can then be adjusted so that each of such struts has a strain within the target range under a predetermined operating load. The resultant structure can then be formed using additive manufacturing or the like.

Figure 3A:
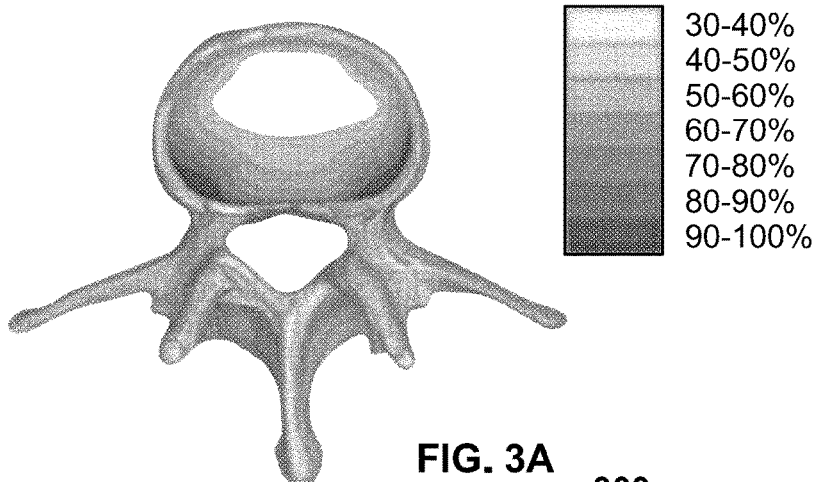
FIG. 3A is a top view of a vertebra illustrating a bone density of a vertebral body thereof.
Figure 3B:
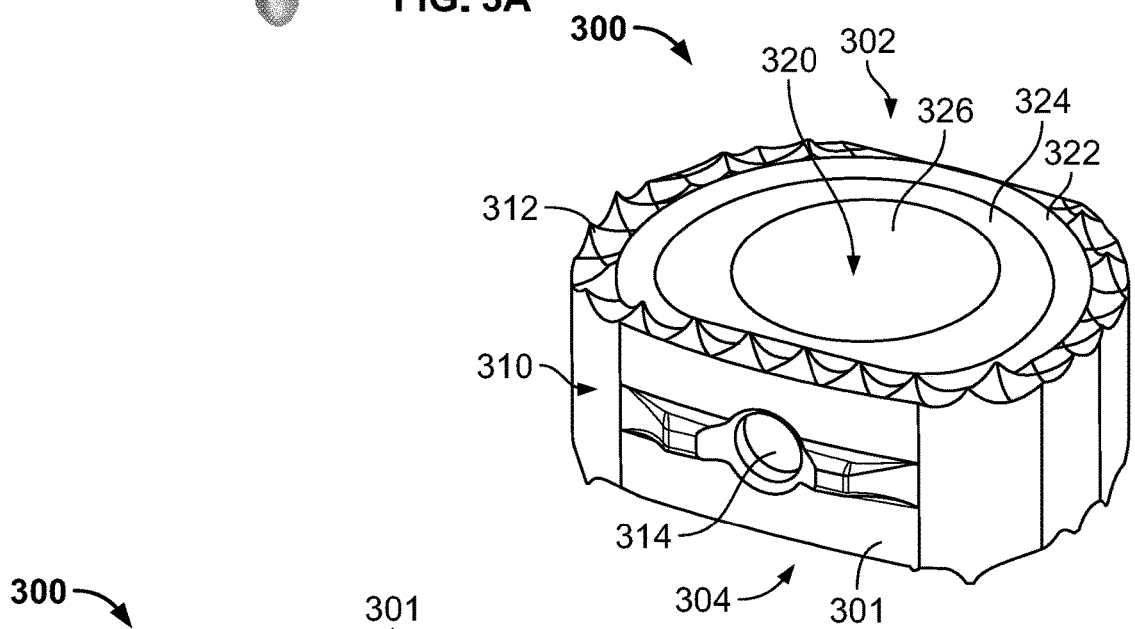
FIG. 3B is a rear perspective view of an IBD according to an embodiment of the present disclosure.
Figure 3C:
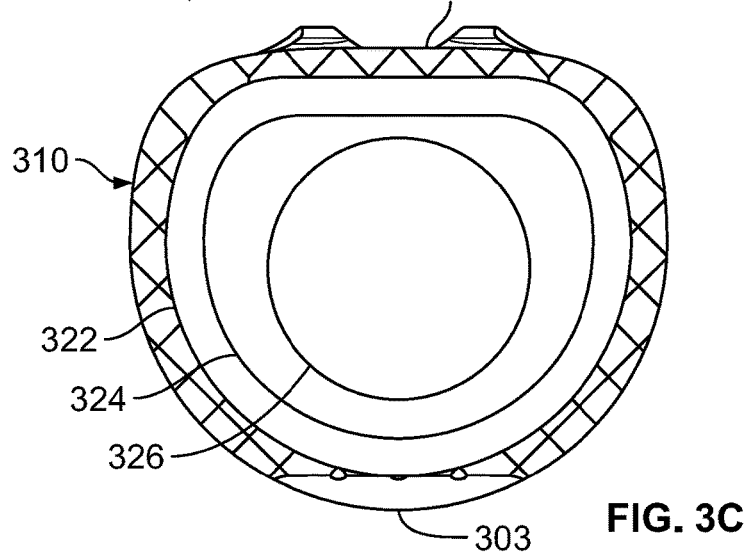
FIG. 3C is a top view of the IBD of FIG. 3B.

FIGS. 3B and 3C depict an IBD 300 according to an embodiment of the disclosure. IBD 300 is particularly suitable for insertion into an intervertebral space, such as a cervical disc space, via an anterior approach. IBD 300 generally includes a solid frame or outer wall 310 and a porous core 320 that includes a porous structure with a varying porosity.

As shown, outer wall 310 extends about porous body or core 320 and forms a perimeter thereof. Outer wall 310 includes teeth or spikes 312 at superior and inferior sides 302, 304 thereof. Such spikes 312 generally extend above and below porous core 320 so that such spikes 312 can engage vertebral bodies that are disposed above and below IBD 300 to help prevent movement of IBD 300 while bone grows into porous core 320. Outer wall 310 also includes an engagement opening 314 at a trailing end 301 of IBD 300. Such engagement opening 314 is configured to connect to a corresponding inserter instrument (not shown). Such connection may be a threaded connection, collet connection, or the like. The solid structure of outer wall 310 facilitates such a connection.

Porous core 320 is disposed within the perimeter formed by outer wall 310 and is connected to outer wall 310 such that solid outer wall 310 and porous core 320 form a unitary or monolithic device. This is preferably achieved through additive manufacturing (discussed below) in which porous core 320 and outer wall 310 are formed together layer by layer so that porous core 320 and outer wall 310 form a seamless structure. As shown, porous core 320 includes a first section or ring 322, a second section or ring 324, and a third section or ring 326. In this regard, first section 322 surrounds second and third sections 324, 326, while second section 324 surrounds third section 326. Sections 322, 324, and 326 may be concentric. In addition, third section 326 may be concentric with a geometric center of outer wall 310. However, it should be understood that the depicted porosity gradients need not be concentric. For example, in some embodiments third section 326 may be biased toward leading end 303 such that third section is positioned much closer to leading end 303 than trailing end 301. Sections 322, 324, and 326 are distinguished by their relative porosities.

As discussed above, porosity is generally a measure of a material's empty space relative to the total space occupied by the material. In contrast, solid outer wall 310 does not have a porosity or has a porosity of substantially zero. In this regard, while outer wall 310 is considered a solid structure, it is recognized that structures that are seemingly non-porous, at least to the naked eye, may have a porosity on a very small scale. Indeed, structures that are manufactured using the additive manufacturing technique of selective laser sintering (discussed below) often have an inherent porosity to the material. Thus, as used herein, the terms non-porous and solid mean a porosity so small or so close to zero as to prohibit bone growth therein.

As mentioned, first, second, and third portions 322, 324, and 326 of porous core 320 are distinguished by their relative porosities. In this regard, sections 322, 324, and 326 have differing porosities. As described above, this can be achieved by varying dimensions of cells that make up the porous structure or by varying the geometric shape of the porous structure's cells. In the particular embodiment depicted, the porosities vary so that porosity increases toward the center of core 320. As such, third section 326 has a greater porosity than first and second sections 322, 324, and second section 324 has a greater porosity than first section 322. In one particular example, third section 326 may have a porosity of 80%, second section 324 may have a porosity of 60%, and third section 326 may have a porosity of 40%. However, in other embodiments the first, second, and third sections 322, 324, and 326 may have a respective porosity within the range of about 10% to 90% with an average pore width/diameter between 20-1000 microns.

The above described arrangement of increasing porosity toward the center of IBD 100 mimics the bone density of a natural vertebral body, as illustrated by the bone density map of FIG. 3A. As shown, the lowest density of bone is located in the center of the vertebral body with an increasing density towards the outer wall of the vertebral body. This correspondence to the natural bone density helps facilitate bone growth in that the porosity of implant 300 closely aligns with the natural porosity of the vertebral body. In addition, mimicking the natural bone densities of vertebrae positioned above and below IBD 300, particularly where IBD is strain optimized as discussed above, reduces the overall stiffness of IBD as compared to an IBD that does not have varying porosities so as to reduce the likelihood of stress shielding.

It should be understood that, while three sections of porous core 320 are shown, porous core 320 can include more or less porous sections. For example, if more fidelity or precision is desired to match a particular patient's bone density, as may be determined through imaging the particular patient's bone or through matching the patient to a corresponding population within a bone database, porous core 320 can have more than three sections. For example, porous core can have 4 to 10 sections of differing porosities. Moreover, as discussed above, a gradual increase in porosity may be achieved by increasing the lengths of the struts forming the cells of the porous core so that there is almost an indiscernible number of sections of the porous core. Conversely, abrupt changes between each section can be achieved by having differing cell geometries for each section. For example, first section may be comprised of diamond cubic cells, second section may be comprised of single cubic cells, and third section may be comprised of body-centered cubic cells.

Figure 4A:
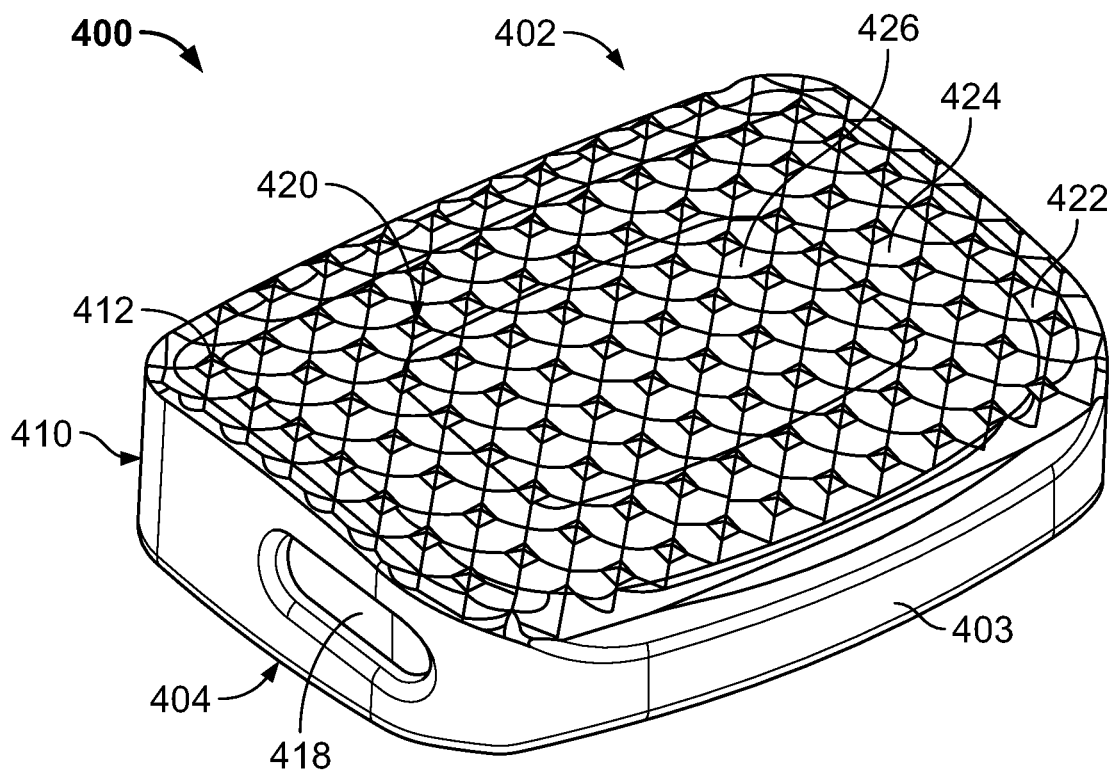
FIG. 4A is a front perspective view of an IBD according to another embodiment of the present disclosure.
Figure 4B:
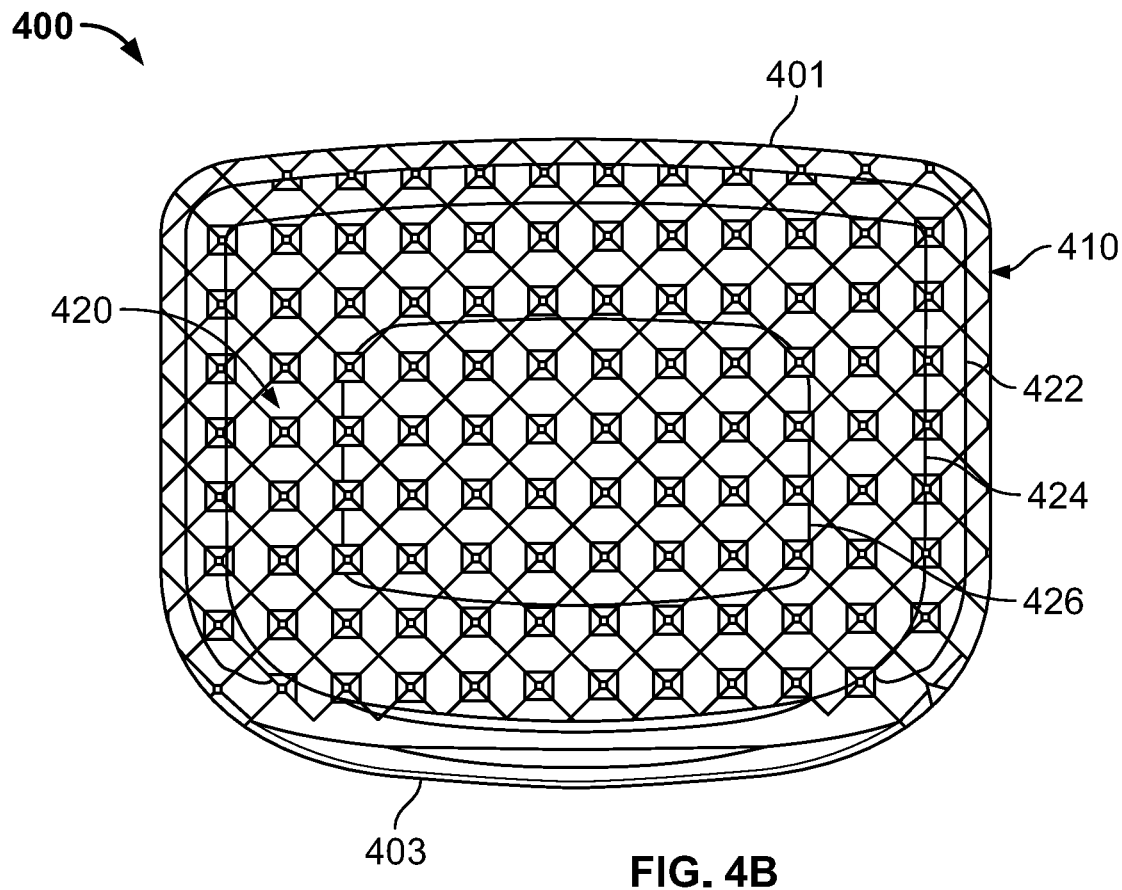
FIG. 4B is a top view of the IBD of FIG. 4A.
Figure 4C:
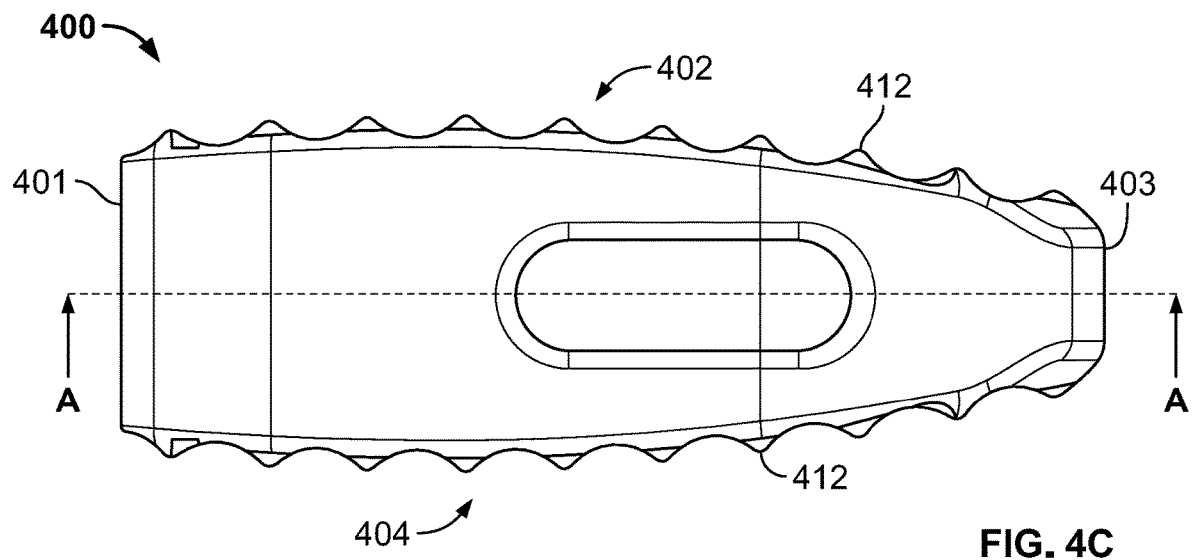
FIG. 4C is side elevational view of the IBD of FIG. 4A.
Figure 4D:
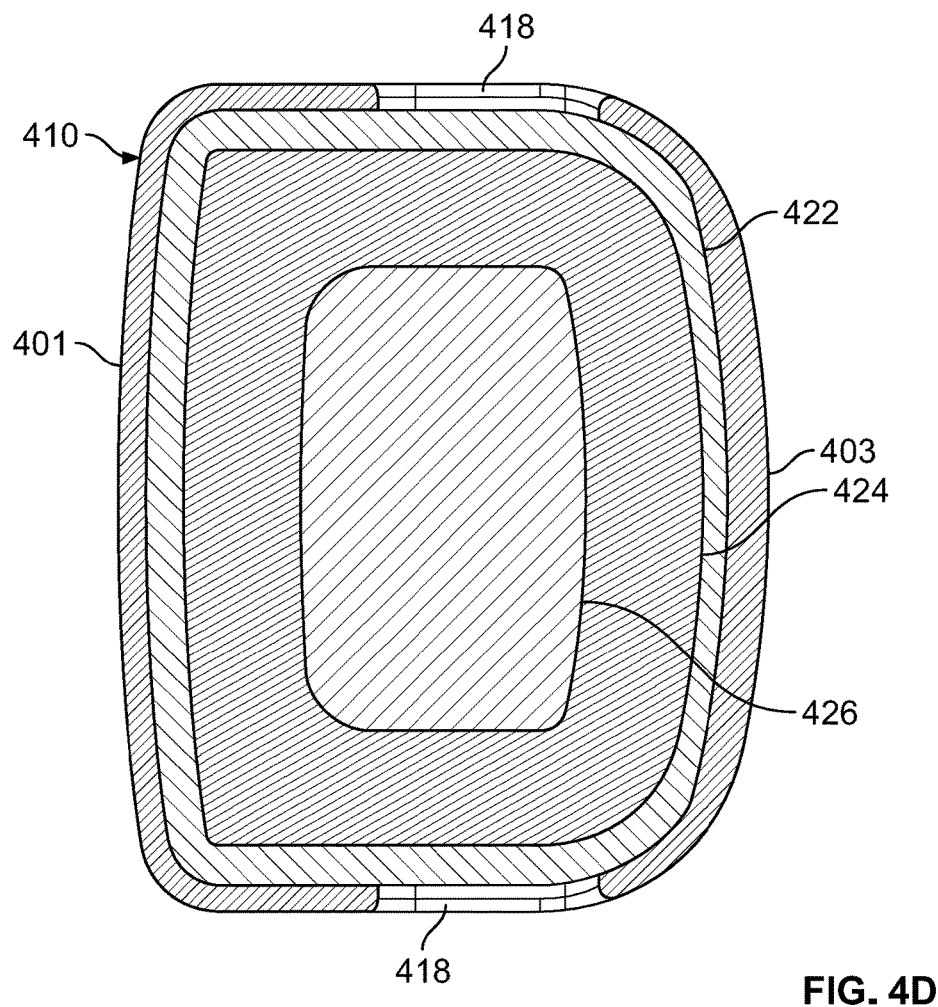
FIG. 4D is a cross-sectional view of the IBD of FIG. 4A taken along line A-A of FIG. 4C.

FIGS. 4A and 4B depict another embodiment IBD 400. For ease of review, like elements are accorded like reference numerals to that of IBD 300, but within the 400-series of numbers. For instance, IBD 400 includes solid outer wall 410 and porous body or core 420. Moreover, porous core 420 of IBD 400 also includes a first section or ring 422, second section or ring 424, and third section or ring 426. The porosities of sections 422, 424, and 426 mirror that of sections 322, 324, and 326 of IBD 300. Thus, the porosity of porous core 420 increases toward the center thereof such that the respective porosities of sections 422, 424, and 426 are within the range of about 30 to 80%.

However, IBD 400 also differs from IBD 300 in a number of ways. First, IBD 400 is particularly suited for implantation into a lumbar disc space via an anterior approach. In this regard, IBD 400 has superior and inferior sides 402, 404 that converge toward each other from a trailing end 401 to a leading end 403 of IBD 400 so as to provide a preferred lordotic angle. Moreover, superior and inferior sides 402, 404 may have a slight convexity to conform to concavities in adjacent vertebral bodies. Further, IBD 400 includes lateral windows 418, which may help reduce the stiffness of outer wall 410. Also, unlike IBD 300, which has spikes 312 extending from outer wall 310, IBD 400 includes spikes 412 extending from both superior and inferior sides 402, 404 of porous core 420. Such spikes 412 are generally non-porous and are embedded in porous core 420 so that spikes 412 extend from upper and lower surfaces thereof. Spikes 412 may extend partially into the respective surfaces of porous core 420. However, spikes 412 may also be constructed as columns that extend full thickness through porous core 420.

Thus, as described above, both IBD 300 and IBD 400 include porous cores 320, 420 that vary in porosity in a radial direction such that when these respective IBD's are implanted, each porous section of a different porosity directly contacts bone to encourage bone to grow therein.

Figure 5A:
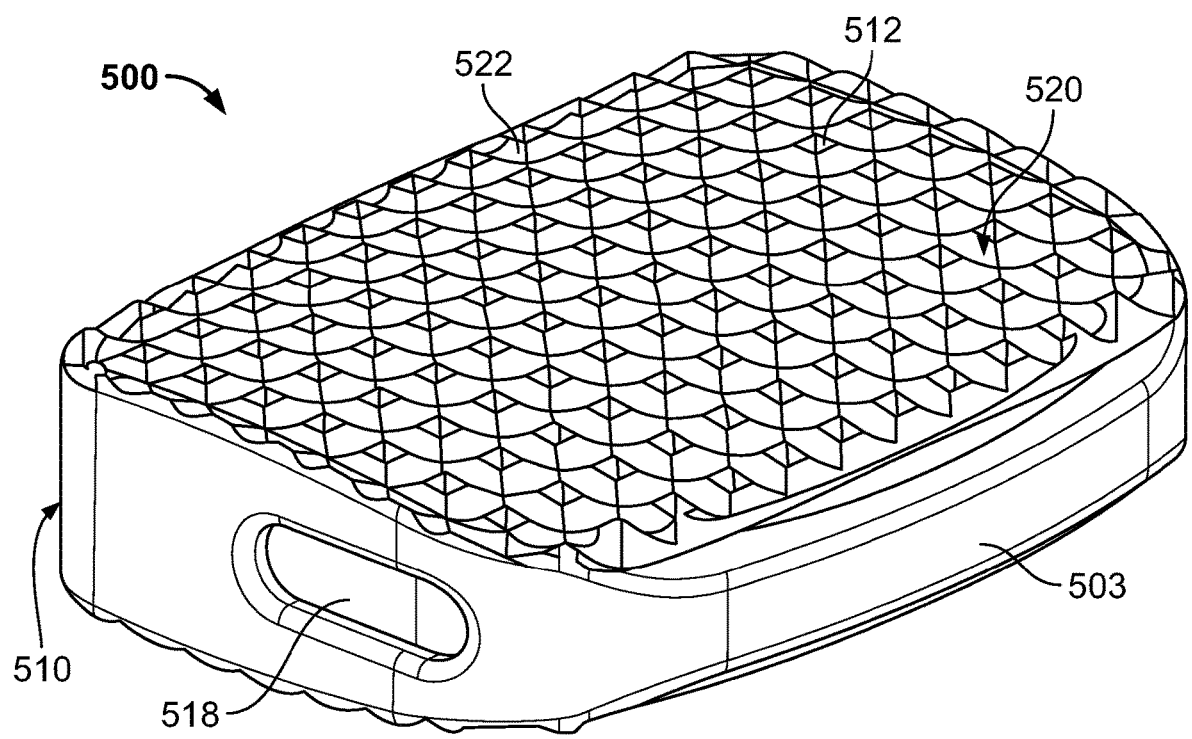
FIG. 5A is a front perspective view of an IBD according to a further embodiment of the present disclosure.
Figure 5B:
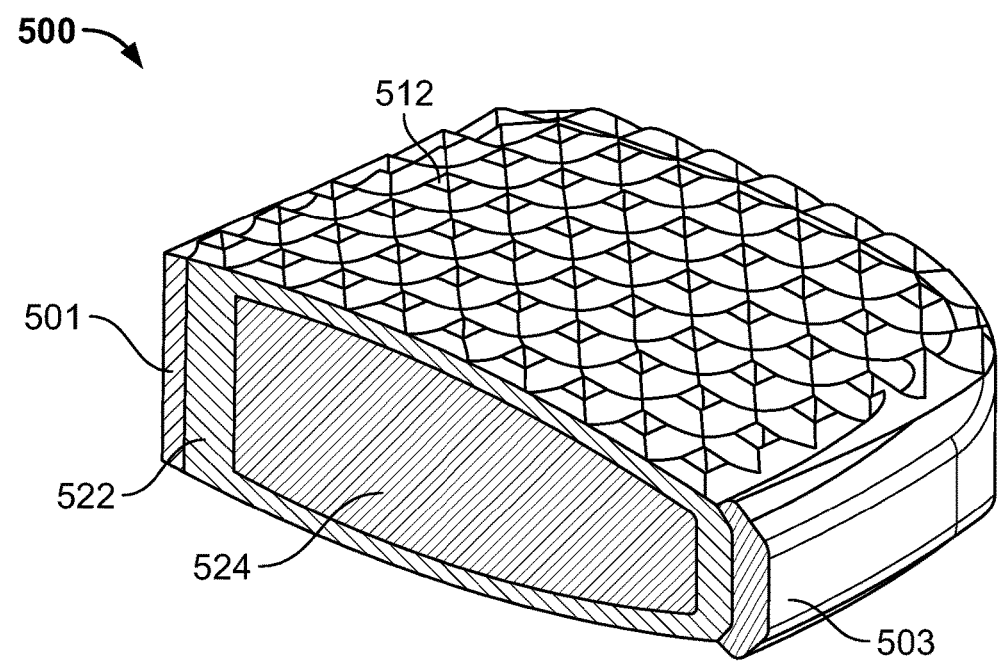
FIG. 5B is a sagittal cross-sectional perspective view of the IBD of FIG. 5A taken along a midline thereof.
Figure 5C:
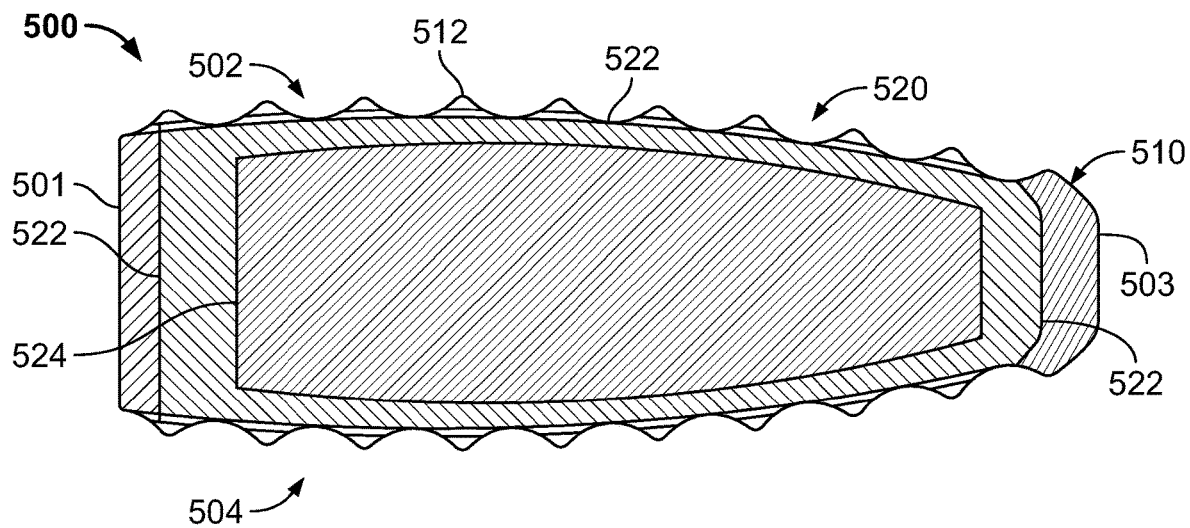
FIG. 5C is a sagittal cross-sectional view of the IBD of FIG. 5A taken along a midline thereof.

In contrast, FIGS. 5A-5C depict a further IBD embodiment 500. IBD 500 is similar to IBD 400 in that it is particularly configured for implantation into a lumbar disc space via an anterior approach and has a lordotic taper, as best seen in FIG. 3C. In addition, IBD 500 includes a solid outer wall 510, porous body or core 520, and spikes 512 embedded in inferior and superior sides 502, 504 of porous core 520. However, unlike porous core 420, porous core 520 includes a first section or outer layer 522 that entirely surrounds a second section or inner layer 524 so that when IBD 500 is implanted, only outer layer 522 of porous core 520 is exposed to adjacent vertebrae.

Inner and outer layers 522, 524 are distinguishable based on their relative porosities where inner layer 524 preferably has a higher porosity than outer layer 522. For example, in one embodiment inner layer 524 may have a porosity of 60%, and outer layer 522 may have a porosity of 40%. However, the respective porosities of inner and outer layers 524, 522 can be within the range of about 30 to 80% with an average pore width/diameter between 20-1000 microns. Thus, for example, outer layer 522 may have a porosity of 10% and inner layer 524 may have a porosity of 90%. The lower porosity outer layer 522 helps provide strength to IBD and a strong initial fusion with bone to help resist movement of IBD 500 within the disc space in response to flexion, extension, torsion, and bending range of motions. However, higher porosity inner layer 524 facilitates strong long term bone ingrowth by providing more volume for bone proliferation than outer layer 522. Thus, inner layer 524, while potentially taking longer to facilitate bone growth, provides a stronger long term connection than outer layer 522.

Moreover, while only an inner and outer layer 524, 522 are depicted, in some embodiments of IBD 500, further layers can be provided so that the transition to the greatest porosity inner layer is more gradual. For example, IBD 500 may have three or four layers where each successive layer toward the center of IBD 500 has a larger porosity.

Figure 6A:
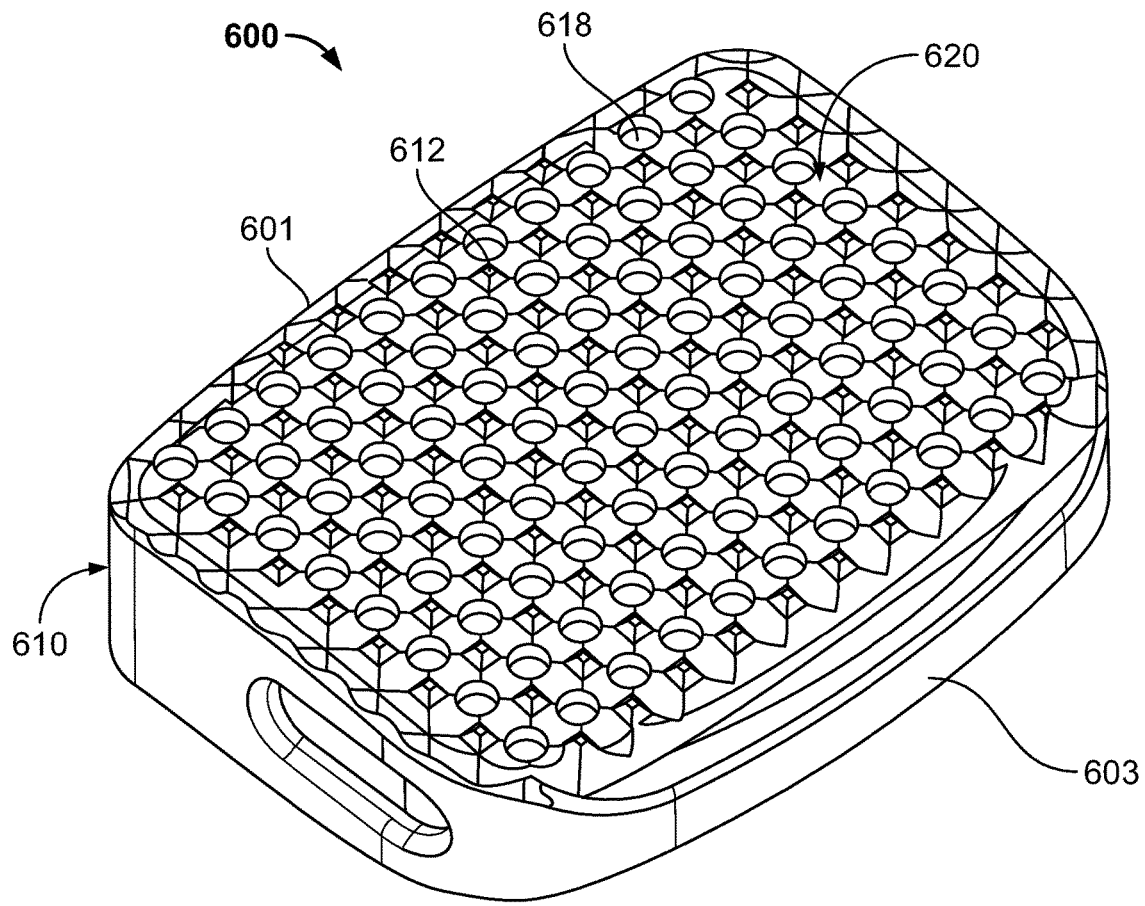
FIG. 6A is a front perspective view of an IBD according to an even further embodiment of the present disclosure.
Figure 6B:
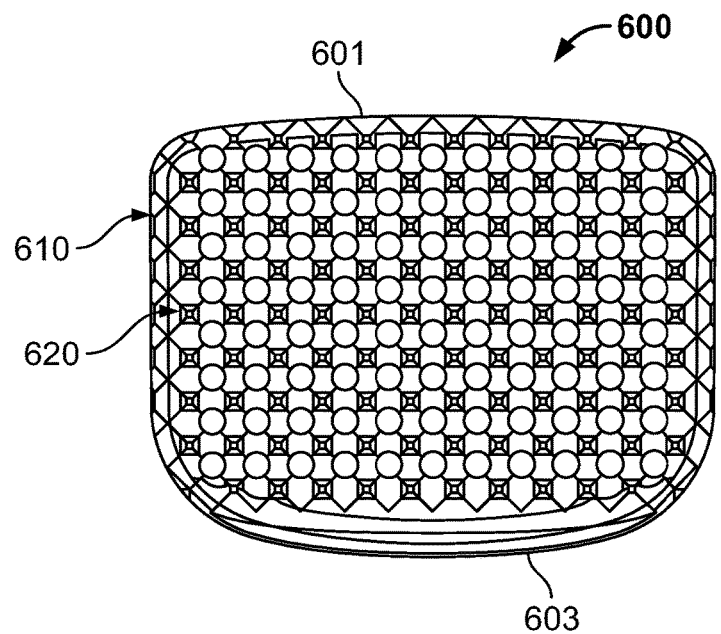
FIG. 6B is a top view of the IBD of FIG. 6A.
Figure 6C:
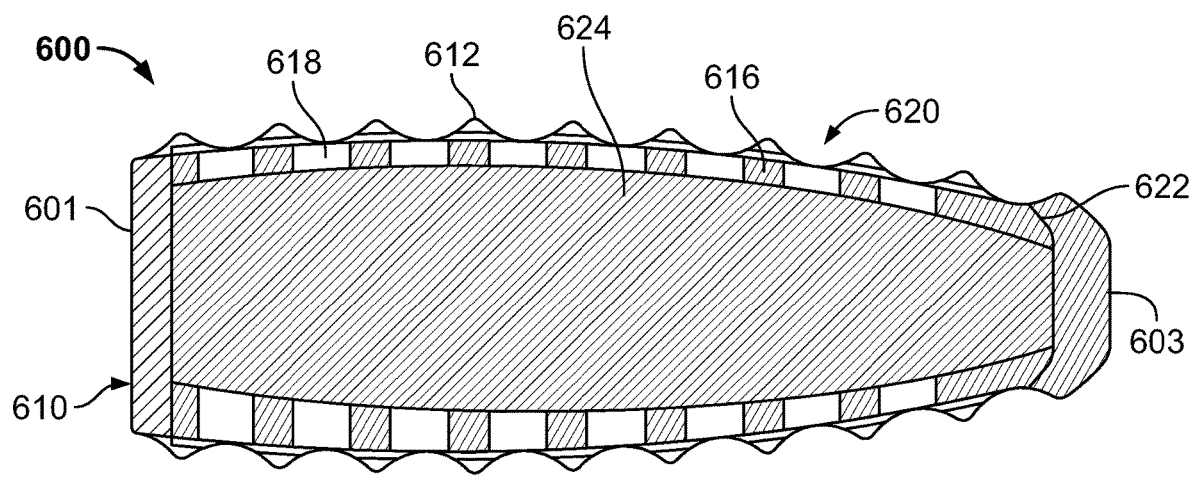
FIG. 6C is a sagittal cross-sectional view of the IBD of FIG. 6A taken along a midline thereof.

FIGS. 6A-6C depict another embodiment IBD 600, which is similar to IBD 500. For ease of review, like elements are accorded like reference numerals to that of IBD 500, but within the 600-series of numbers. For instance, IBD 600 includes solid outer wall 610 and porous body or core 620 where porous core 620 includes an inner layer with a larger porosity than an outer layer. However, IBD 400 differs from IBD 600 in that outer layer, in addition to having a porous structure comprised of a plurality of adjoined cells, includes through-holes 618 of a much larger size than the porous structure that makes up outer layer 622. In this regard, outer layer 622 forms a grid-like pattern in which outer layer 622 comprises intersecting beams 616 of porous material and in which spikes 412 project from outer layer 622 at the intersections of such beams 616. This configuration, just as in IBD 300, allows for a strong initial ingrowth connection between outer layer 622 and bone. However, through-holes 618 facilitate enhanced blood flow to inner layer 624 over that of IBD 500. Moreover, through-holes 617 facilitate accelerated contact between bone cells and inner layer 624 by providing a path of reduced resistance for the movement of such cells. Again, it is contemplated that further layers may be included in IBD 600. In addition, it is contemplated that outer layer 622 may not have a porous structure separate and apart from the through-openings 618 and instead may be a solid grid that is an extension of solid outer wall 610. However, in such an embodiment, portions of inner layer 624 may extend up into through-openings 618 so as to be disposed close to the bone when implanted.

FIGS. 7A-7E depict a further embodiment IBD 700. While IBD 700 is similar to the IBD's described above in that IBD 700 does not include a graft window, IBD 700 differs in that it does not include any exterior solid portions. Instead IBD 700 includes an entirely porous body 700 and a plurality of layers of solid reinforcing members 710 embedded in the porous body or core 720. Porous body 720 can be formed into any shape to suit the particular application, such as for fusion of vertebrae in the cervical or lumbar spine. The embodiment depicted is particular suited for application to a lumbar spine. Moreover, the porosity of porous body 720 may be uniform throughout or may vary as described above with respect to IBD 500 and 600.

Figure 7A:
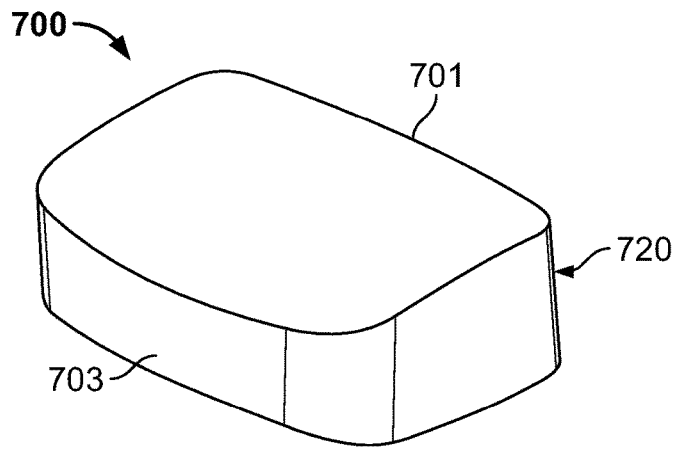
FIG. 7A is a front perspective view of an IBD according to a yet further embodiment of the present disclosure.
Figure 7B:
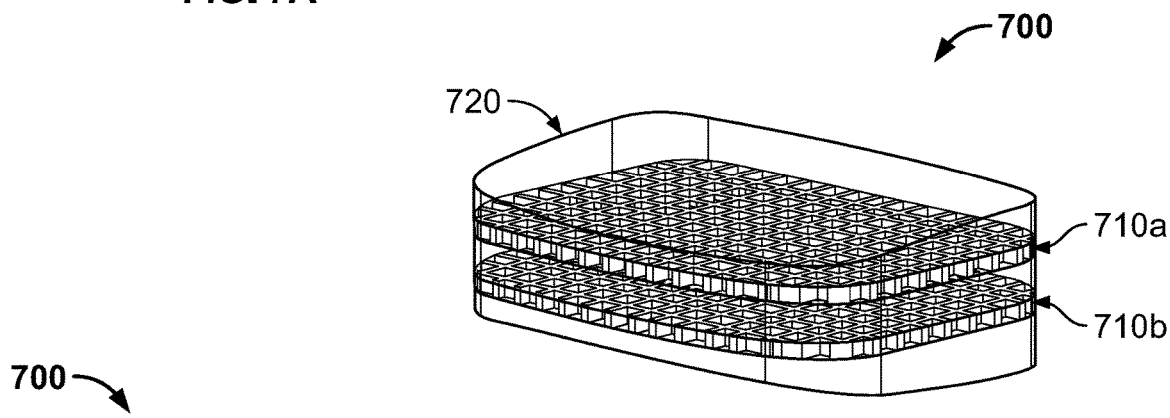
FIG. 7B is a partially transparent view of the IBD of FIG. 7A.
Figure 7C:
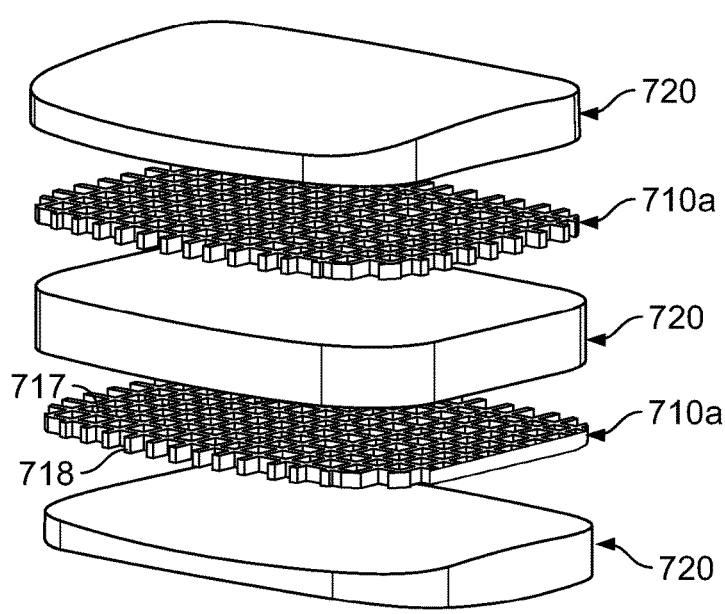
FIG. 7C is an exploded view of the IBD of FIG. 7A.
Figure 7D:
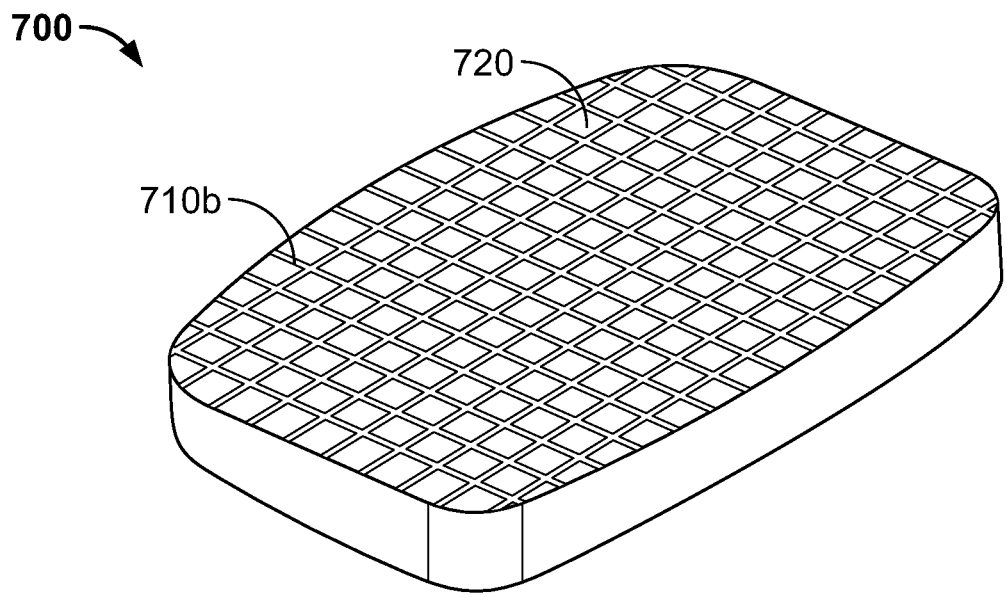
FIG. 7D is a transverse cross-sectional view of the IBD of FIG. 7A.
Figure 7E:
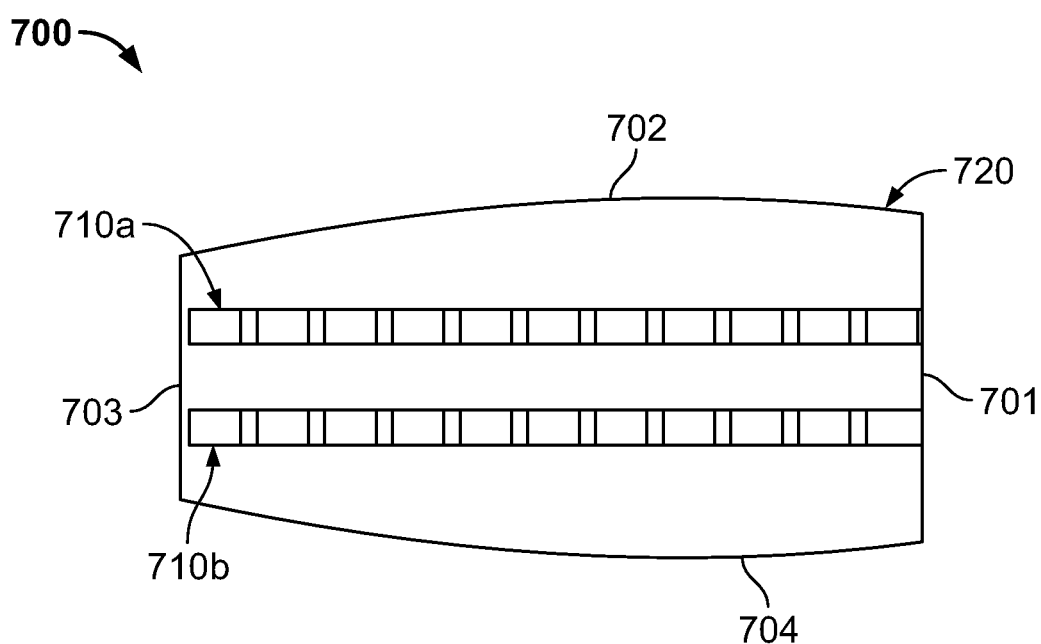
FIG. 7E is a sagittal cross-sectional view of the IBD of FIG. 7A.

In the embodiment depicted, the solid reinforcing members 710a-b are gridded structures that each include a plurality of perpendicularly intersecting beams 718 that form through-openings 717 that extend in a superior-inferior direction. Reinforcing members 710a-b are embedded within porous body 720 at predetermined intervals such that they each extend in respective planes that are transverse to a spinal axis when IBD 700 is implanted. In this regard, beams 718 of reinforcing members 710a-b extend in directions which are generally perpendicular to the compressive loads normally imposed on IBD 700 within a disc space. Porous body 720 completely encompasses reinforcing members 710a-b such that porous body 720 extends through through-openings 717 of reinforcing members 710a-b, as best shown in FIG. 7D. While two reinforcing members 710a-b are depicted, the number of reinforcing members 710 and the spacing therebetween can increase or decrease as needed to provide optimal support. IBD 700 is a composite-like structure in which the tensile strength of solid reinforcing members 710*a-b* increases the shear strength of porous body 710, which tends to have more strength in compression than in tension. Thus, when IBD 700 is axially loaded, the gridded beams 718 of reinforcing members 710*a-b* act in multiple directions to help alleviate stress in the areas under tension. In this regard, reinforcing members 710*a-b* can have different configurations depending on the directions of highest tensile stress. For example, reinforcing members 710*a-b* can be oriented vertically or obliquely within IBD, rather than horizontally as shown. In another example, reinforcing members 710*a-b* may comprise concentric rings of solid material with elongate beams extending radially from a center of the rings. Moreover, the internal reinforcement provided by reinforcement members 710*a-b* help assess fusion via radiographic imagery as new bone growth is not obscured by outer solid structures and new bone growth can be measured relative to the known depth of reinforcement members 710*a-b* within porous body 720.

While various windowless IBD's are described above as having differing porous and solid structural configurations, other windowless IBD's may be modified to have similar configurations. Some of such windowless IBD's are described in U.S. Application No. 62/560,910, which is hereby incorporated by reference herein in its entirety. Moreover, while certain solid and porous configurations are described above in association with certain types of IBD's, such as certain cervical and lumbar IBD configurations, it should be understood that the above described solid and porous configurations can be implemented in any type of spinal implant including those that can be implanted in a cervical or lumbar spine via anterior, posterior, lateral, and posterolateral approaches, for example. Also, such configurations may be implemented in other types of orthopedic devices, such as tibial and femoral components of a knee prosthesis, femoral and acetabular components of a hip prosthesis, and humeral and glenoid components of a shoulder prosthesis, to name a few. In this regard, such implants often have porous bone interfacing surfaces which, as described above, can have varying porosities to match the bone density of associated bones, or varying porosities in which an outer layer has a lower porosity to establish a strong initial connection and a higher porosity inner layer to facilitate a stronger long term connection.

Figure 8:
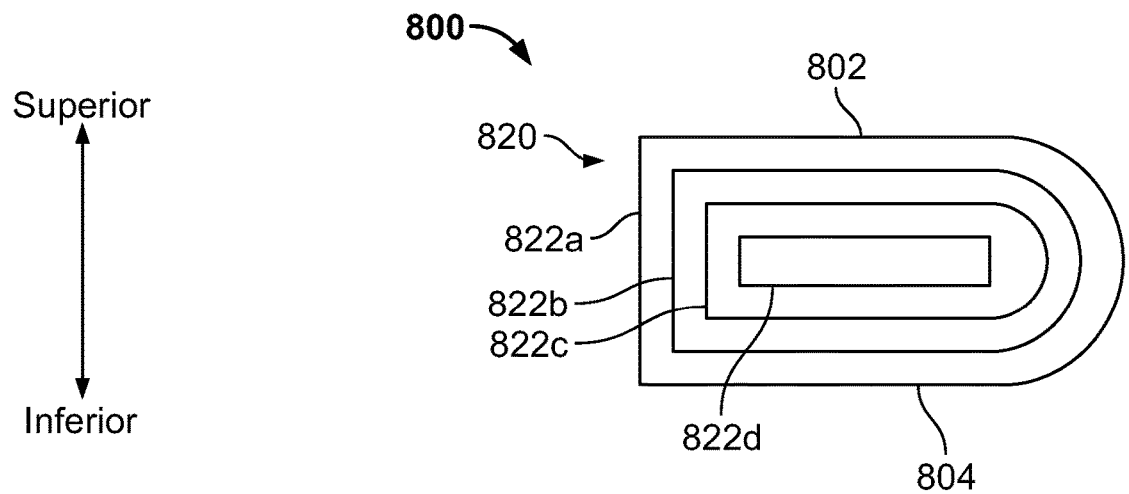
FIG. 8 is an elevational cross-sectional view of an IBD according to a further embodiment of the present disclosure.

FIG. 8 depicts a cross-section of another one of such windowless IBD's. IBD 800 is similar to IBD 500 and 600 in that it includes multiple layers of a porous body or core 820 where each successive layer has a different porosity. In addition, while not shown, IBD 800 may include a solid outer wall and may also include solid projections or other bone engaging projections embedded in its porous structure, such as at superior and inferior sides 802, 804 of IBD 800. However, unlike IBD's 500 and 600, the porosity of IBD 800 increases toward the inner layer 822*d* of porous structure 820. Thus, in the embodiment depicted, first layer 822*a* has the highest porosity while fourth layer 822*d* has the lowest porosity. Also, second layer 822*b* has a higher porosity than third layer 822*c*. For example, first layer 822*a* may have a porosity of 70%-80%, second layer 822*b* may have a porosity of 60%-70%, third layer 822*c* may have a porosity of 50%-60%, and fourth layer 822*d* may have a porosity of 30%-50%. As discussed in more detail above, this change of porosity between each layer 822*a-d* can be achieved by changing the length of the struts of the cells comprising each layer 822, and/or by changing the geometric shape of the cells that make up the layers 822*a-d*. Thus, for the embodiment depicted, the first layer 822*a* may have cells with longer struts than second, third and fourth layers 822*b-d*. Alternatively, first layer 822*a* may comprise diamond cubic cells, second layer 822*b* may comprise simple cubic cells, third layer 822*c* may comprise body-centered cubic cells, and forth layer 822*d* may comprise face centered cubic cells, for example.

The configuration of IBD 800 in which porosity decreases toward the center of IBD 800 allows a bioactive material, such as sol-gel bioactive glass (e.g., silicate, borate, and borosilicate bioglasses) or sol-gel derived bone graft, to be dispersed into the porous structure 820 of IBD 800 to enhance bone growth within the porous structure 820. Such bioactive material is generally provided in the form of particles or beads that have a known size distribution. The pore size of each layer of IBD 800 may be tuned so that the chosen particle size of the bioactive material can penetrate the desired volume of IBD 800. For example, in one embodiment first and second layers 822*a-b* may have an average pore size greater than the particle size of a bioactive material, while third and fourth layers 822*c-d* may have an average pore size less than the particle size of the bioactive material. In such embodiment, the bioactive material can only be dispersed into the first and second layers 822*a-b*. In another embodiment, the pore size of the layers 822*a-d* can be tuned so that the bioactive material can only penetrate first layer 822*a*, while in other embodiments the pore size of the layers 822*a-d* can be tuned such that the bioactive material can be dispersed through all the layers 822*a-d*. In addition to allowing bioactive materials to be dispersed through one or more layers of IBD 800, the configuration of decreasing porosity toward the center of IBD 800 allows initial blood flow to penetrate into the deeper layers of IBD 800. Such blood flow can accelerate time to fusion while the internal strength of the lowest porosity layers of IBD can help resist subsidence.

Figure 9A:
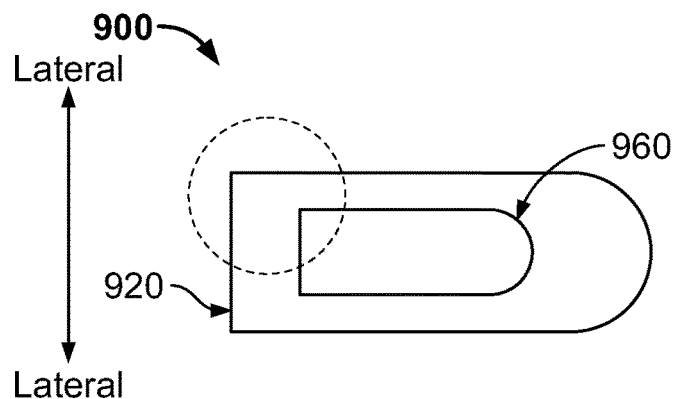
FIG. 9A is a top view of an IBD according to still another embodiment of the present disclosure.

FIG. 9A depicts another embodiment IBD 900 according to the present disclosure. Unlike the previously described IBD's, IBD 900 includes a graft window 960. In addition, IBD 900 includes a porous body or wall 920 or boundary surrounding graft window 960. Thus, graft window 960 is in communication with the pores of porous wall 920. While not shown, IBD 900 may further include a solid outer wall surrounding porous wall 920 and bone engaging projections, like those of IBD's 400 and 500, embedded in porous wall 920.

Figure 9B:
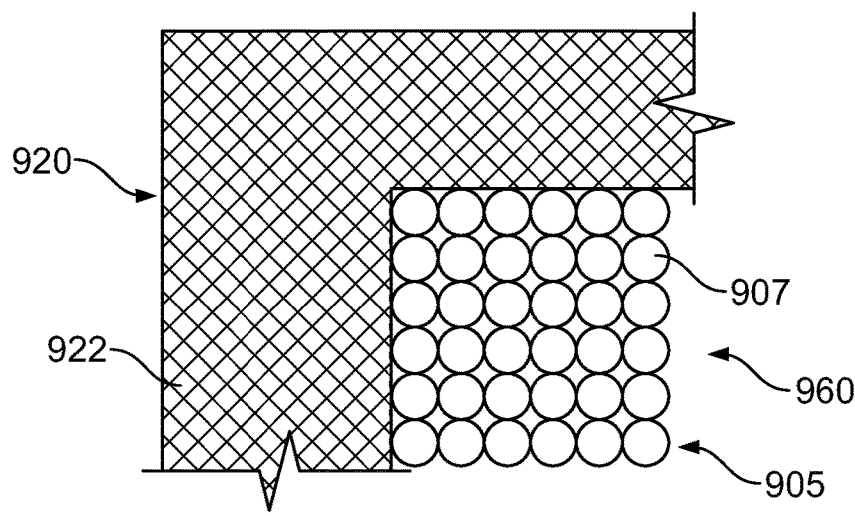
FIG. 9B-9D are enhanced views of an encircled portion of the IBD of FIG. 9A depicting various configurations thereof in conjunction with a bioactive material.
Figure 9C:
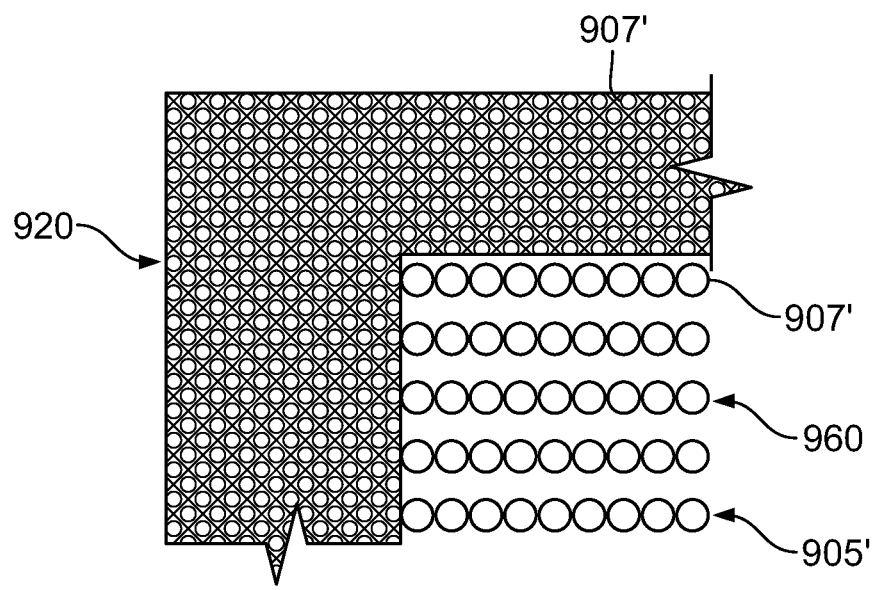
Figure 9D:
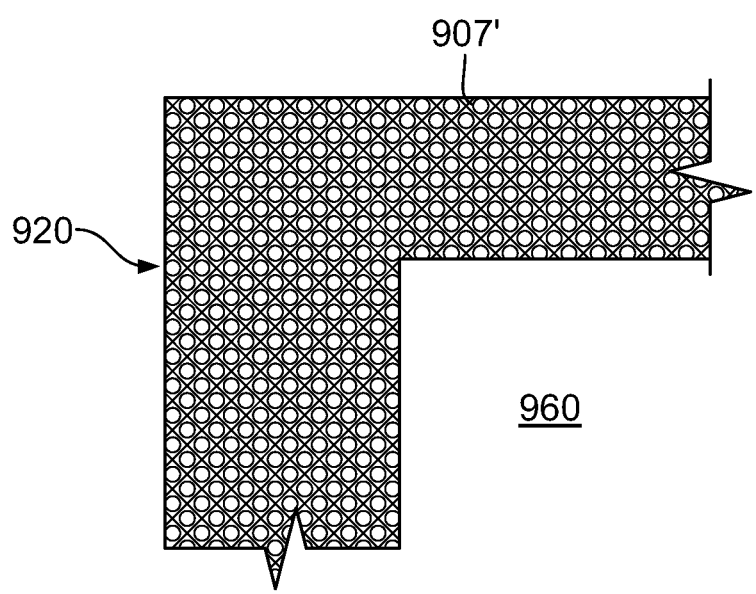

FIGS. 9B to 9D depict various configurations of IBD 900 in conjunction with a bioactive material, such as the bioactive materials mentioned above with respect to IBD 800. In particular, FIG. 9B depicts a portion of porous outer wall 920 and graft window 960. In this configuration, the bioactive material 905 is selected such that the size of the beads or particles 907 are larger than the pore size of porous wall. For example, in one embodiment, the particle size of bioactive material 905 may be at least 500 microns. In this regard, the size of pores 922 may be less than 500 microns, but preferably 20 to 450 microns. As such, bioactive material 905 may only be deposited into the graft window as the relatively large particles 907 are prohibited from being received by pores 922. Moreover, pores 922 of porous wall 920 directly communicate with graft window 960 so that bone can proliferate from graft window 960 into the adjacent porous structure.

In the configuration shown in FIG. 9C, bioactive material 905' is selected to have a particle size smaller than pores 922 of the porous structure 920. Preferably the pore size of porous structure 920 is 100 microns greater than the published range of the bioactive material's particle size, or 500 microns greater than its published mean particle size. For example, in one embodiment particles 907' may have a particle size of 100 microns or less. In this regard, the pore size of the porous structure 920 of implant 900 may be greater than 100 microns, but preferably between 200 to 1000 microns. Thus, in this configuration, bioactive particles 907' penetrate the porous structure 920 so as to be dispersed therein. In addition, as shown, the bioactive material 905' fills graft window 960. It is also contemplated, that IBD 900 may not include a graft window and instead may include the porous material in its place. In such embodiment, the bioactive material 905' may be dispersed throughout such a porous structure.

The configuration depicted in FIG. 9D is similar to that of FIG. 9C in that the particle size of the bioactive material is selected to be less than the pore size of the implant's porous structure 920. However, in this configuration, graft window 960 is plugged while IBD 900 is impregnated with the bioactive material, and then later unplugged so that graft window 960 does not include the bioactive material. In this regard, the bioactive material only populates porous structure 920 of IBD 900. Bone graft material, such as demineralized bone matrix or bone morphogenetic protein, can then be packed into graft window 960, if desired.

Figure 9E:
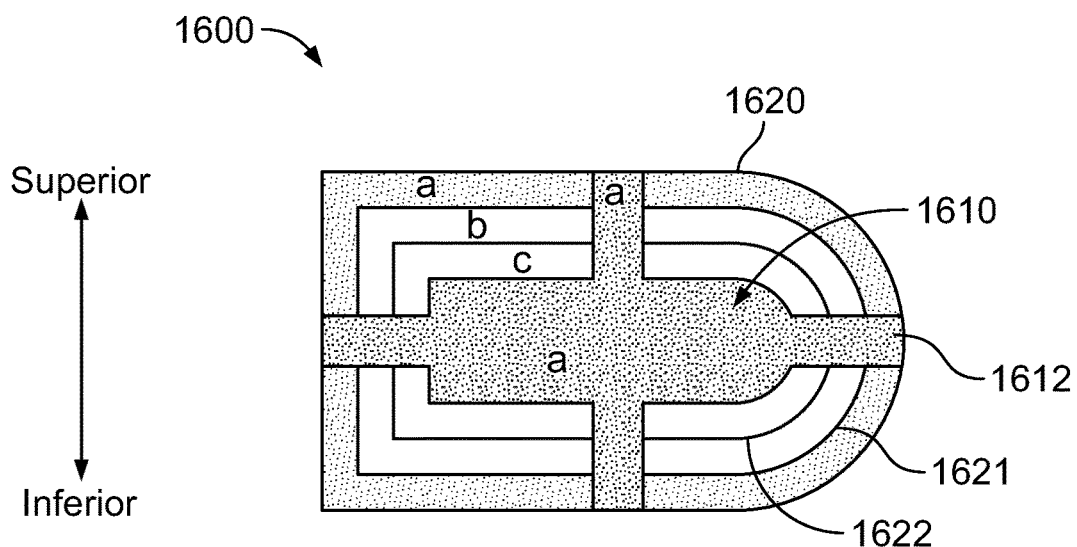
FIGS. 9E and 9F are cross-sectional side views of separate IBD embodiments in conjunction with a bioactive material taken along a midline of the IBD's.
Figure 9F:
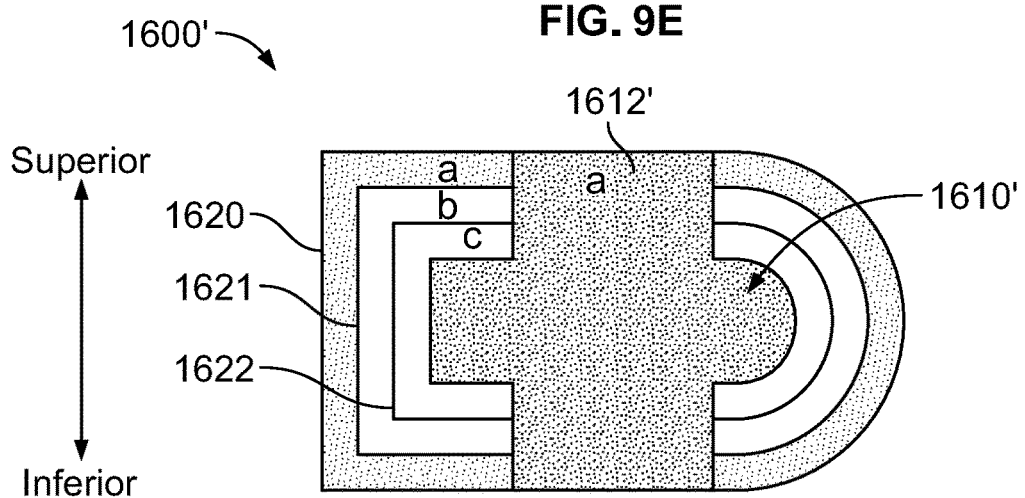
Figure 9G:
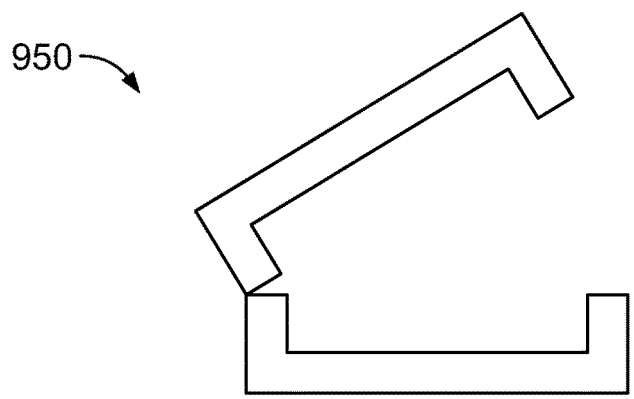
FIG. 9G is a schematic view of an IBD mold according to an embodiment of the present disclosure.

In a method of manufacture, the IBD's described above can be impregnated with bioactive materials by loading the IBD into a mold, jig, or housing that substantially conforms to the IBD, such as the mold 950 depicted in FIG. 9G. The bioactive particles, preferably in a sol-gel state, are then injected into the mold, jig, or housing under greater than ambient pressure so as to force the bioactive material into the appropriately sized pores of the porous structure and/or the graft window of the implant. The solution (i.e., sol-gel) is then allowed to solidify. Thereafter, the implant is demolded or otherwise removed from the jig or housing. The impregnated IBD may then be post processed to remove an outer layer of the bioactive material so that the porous structure is exposed at the bone interfacing sides of the IBD. Alternatively, the injection molded surface of bioactive material, which may coat the outer surfaces of the porous structure, may not be removed so as to provide a smoother surface for implantation of the IBD. For this method of high pressure injection, it is preferable to select a bioactive material that can be put into a polymer carrier for the injection molding process. Moreover, this process is not limited to IBD's as it can be used on any device that has a porous structure that mates with bone.

FIG. 9E depicts an IBD 1600 according to a further embodiment of the present disclosure. IBD 1600 is similar to IBD 800 in that it is windowless and includes differing layers of porosity. Moreover, outer layer 1620 has a higher porosity than inner layers 1621 and 1622. However, IBD 1600 differs in that inner core has the same porosity as outer layer. Moreover, porous channels or pathways 1612 extend from outer layer 1620 to inner core 1610 such that they are in communication. In this regard, inner layers 1621 and 1622 form discrete segments of relatively lower porosity embedded in a higher porosity substrate. In addition, as described above, IBD 1600 may be impregnated with a bioactive material such that the bioactive material is distributed through outer layer 1620 and inner core 1610 and, in some embodiments, inner layers 1621 and 1622. However, inner layers 1621 and 1622 may have a porosity that prevents the bioactive material from being distributed therein. This configuration helps control the regions in which the bioactive material can be distributed. In addition, IBD 1600 helps enable quick bone growth for initial fixation and long-term ingrowth.

FIG. 9F depicts another alternative embodiment IBD 1600", which is similar to IBD 1600'. As shown in FIG. 9E, IBD 1600' depicts pathways 1612 extending superiorly-inferiorly through bone contacting surfaces thereof, but also side-to-side, such as through anterior and posterior ends and/or lateral sides of IBD 1600'. However, unlike IBD 1600', IBD 1600" does not include pathways extending side-to-side and instead includes a single large pathway 1612' that extends superiorly-inferiorly. Such pathway 1612' extends from one bone contacting surface to another and may have the same porosity as outer layer 1620. However, it may also have an even larger porosity than that of layer 1620 so that core 1610' also has a larger porosity than outer layer 1620.

Additional features may be incorporated into orthopedic implants to further enhance bone growth. FIGS. 10A-10D depict a further embodiment IBD 1000 of the present disclosure that includes one such additional feature. IBD 1000 is similar to the windowless IBD's above in that IBD 1000 does not have a graft window and includes a solid outer wall 1010 and porous body or core 1020. However, IBD 1000 includes a plurality of tissue through-channels 1024 that extend longitudinally through a superior side 1002 of IBD 1000 to an inferior side 1004 of IBD 1000, as best shown in FIG. 6C. Through-channels 1024 provide an avenue of least resistance for blood and bone cells to travel through porous structure 1022 between bones or bone fragments. As such, through-channels 1024 are preferably deployed in implants that fuse two or more bones or bone fragments together. In addition, since through-channels 1024 are formed in porous structure 1022, such porous structure 1022 defines through-channels 1024. Thus, blood and bone cells travelling through or residing within through-channels 1024 can access the porous structure 1022 from therein, which further promotes ingrowth.

Figure 10A:
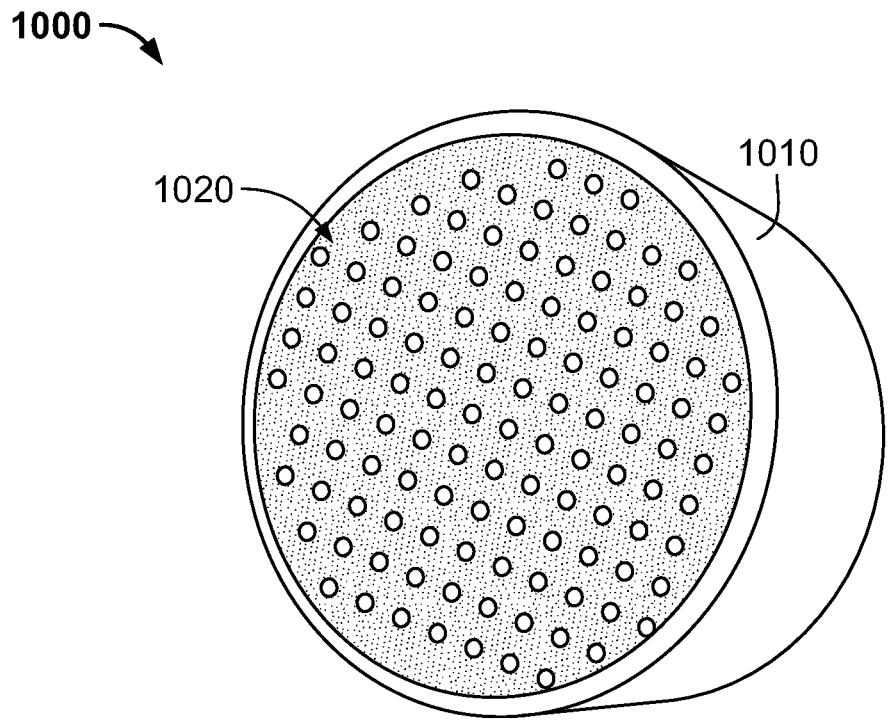
FIG. 10A is a top perspective view of an IBD according to a still further embodiment of the present disclosure.
Figure 10B:
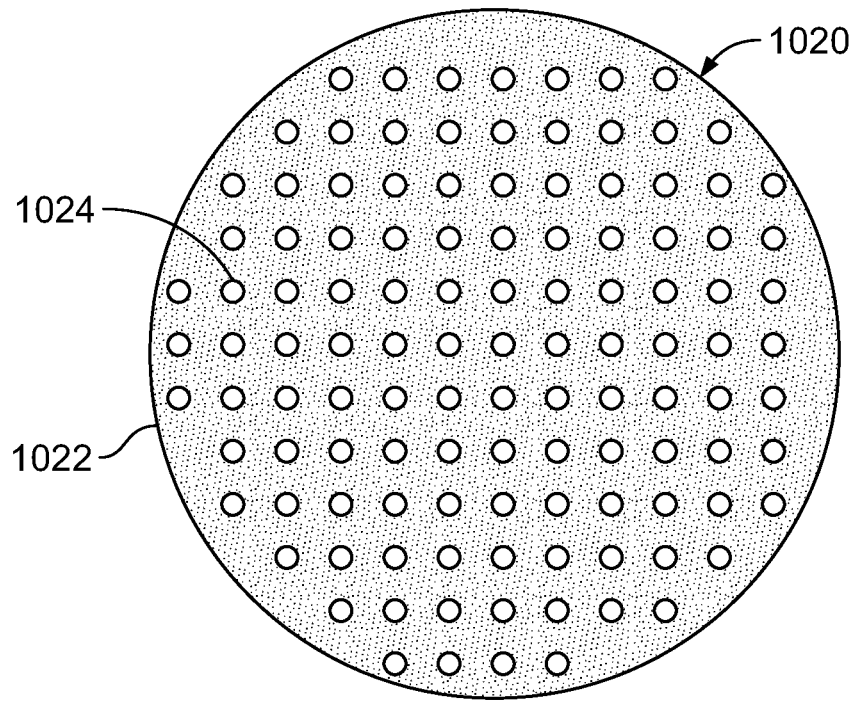
FIG. 10B is a top view of a porous core of the IBD of FIG. 10A.
Figure 10C:
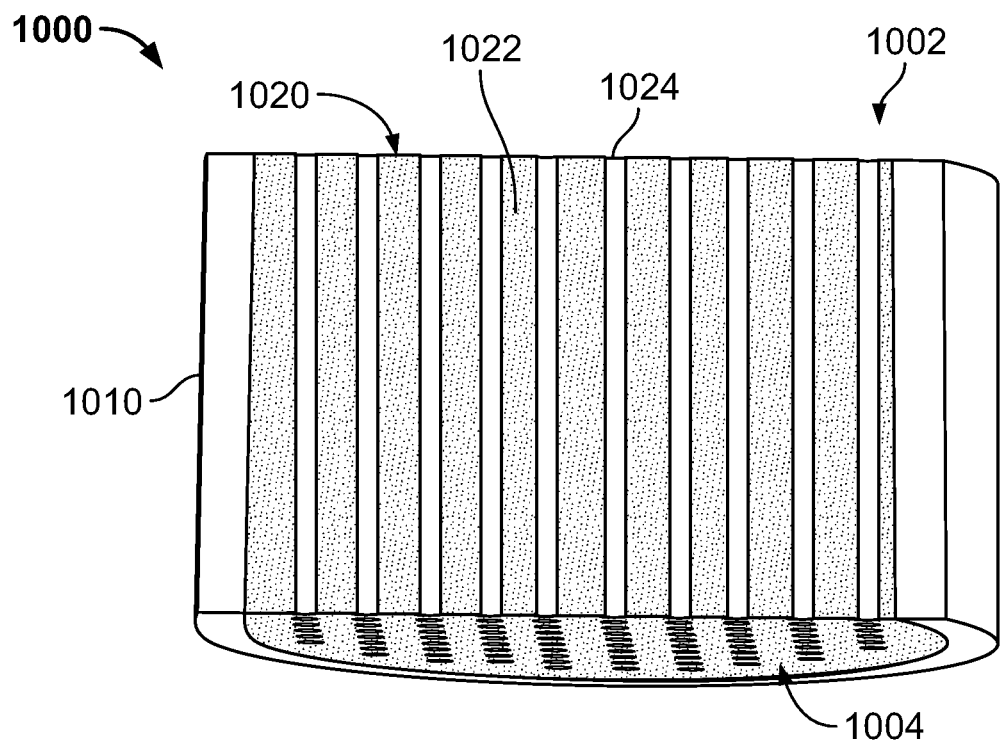
FIG. 10C is a sagittal cross-sectional view of the IBD of FIG. 10A.
Figure 10D:
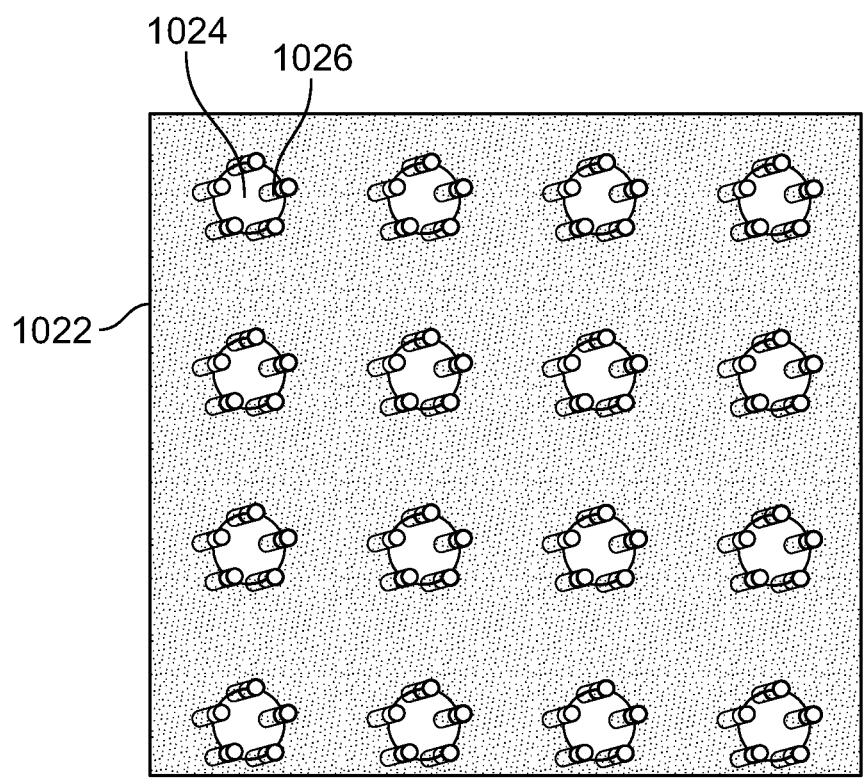
FIG. 10D is an enhanced view of the porous core of the IBD of FIG. 10A.

In this regard, through-channels 1024 are oriented in a direction of desired bone growth. Through-channels 1024 are elongate in that they are significantly longer than they are wide. Through-channels 1024 are distinguishable from the porous structure 1022 surrounding such through-channels 1024 in that through-channels 1024 extend axially along their entire lengths and extend entirely through IBD 1000. In addition, each of through-channels 1024 have a significantly larger cross-sectional dimension than the individual pores of porous structure 1022, as best shown in FIG. 10D. For example, porous structure 1022 of porous core 1020 preferably has a pore size within a range of 100 to 700 microns with a mean pore size range of about 400 to 500 microns and a mean porosity of about 55% to 65%. However, the diameter or cross-sectional dimension of any one of through-channels 1024 is 0.2 to 1 mm.

Also, in the embodiment depicted, solid elongate struts or axial members 1026 extend along the length of each through-channel 1024 and are positioned at a periphery thereof, as best shown in FIG. 10D. For example, five axial members 1026 are positioned about a central axis of each through-channel 1024. However, more or less axial members 1026 are contemplated. Such members 1026 provide connection points for the porous structure 1022 surrounding through-channels 1024 which helps support the interface between the porous structure 1022 and channels 1024, and also provides a surface for initial cell attachment for growth into porous structure 1022. However, as shown, members 1026 do not obscure communication between channels 1024 and the adjacent porous structure 1022. In this regard, longitudinal spaces are defined between adjacent axial members 1026, as best shown in FIG. 10D, so that porous structure 1022 of core 1020 can communicate directly with channels 1024.

Figure 11A:
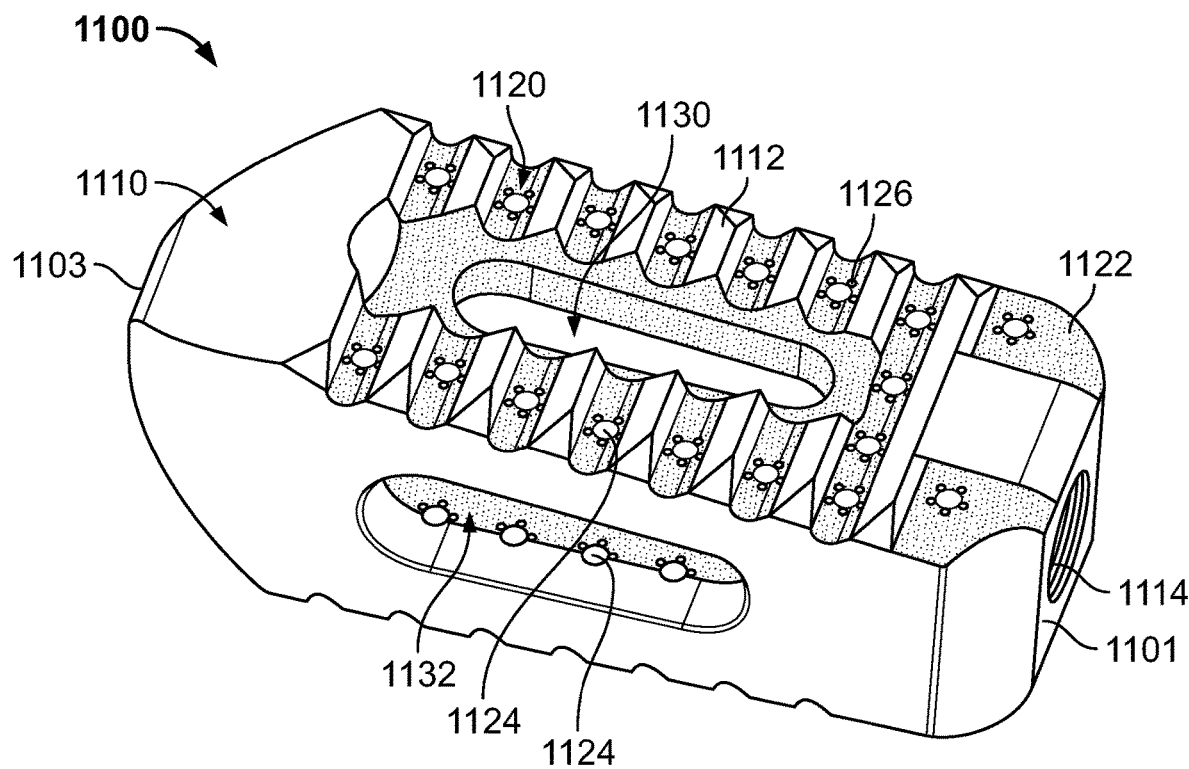
FIG. 11A is a side perspective view of an IBD according to yet another embodiment of the present disclosure.
Figure 11B:
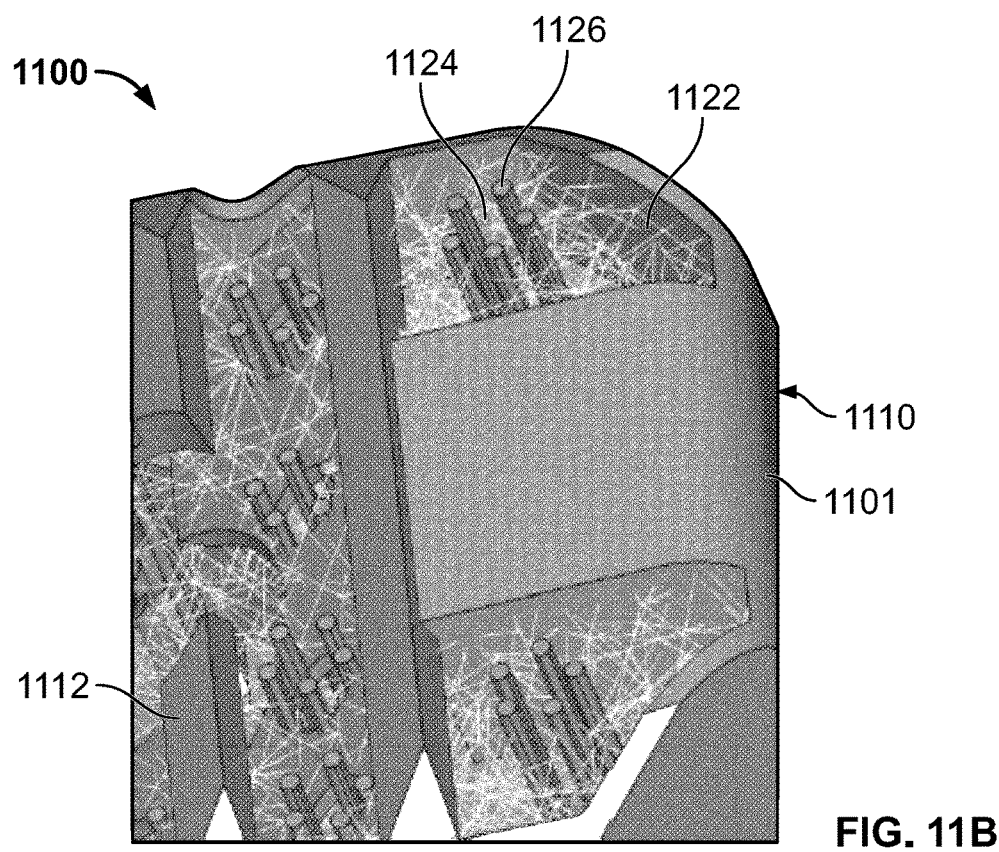
FIG. 11B is an enhanced view of a rear portion of the IBD of FIG. 11A.
Figure 12:
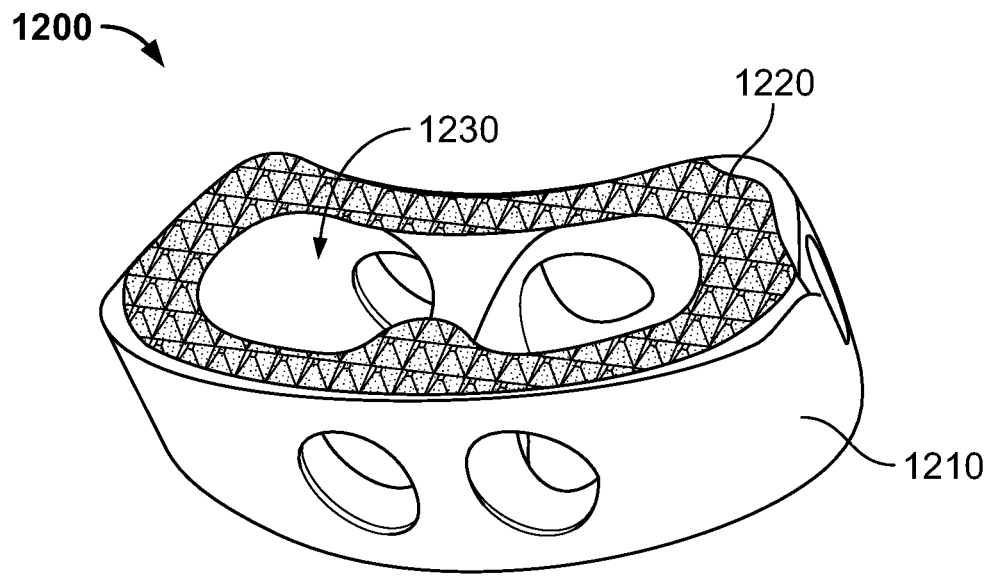
FIGS. 12-15 are perspective views of implants according to even further embodiments of the present disclosure.
Figure 13:
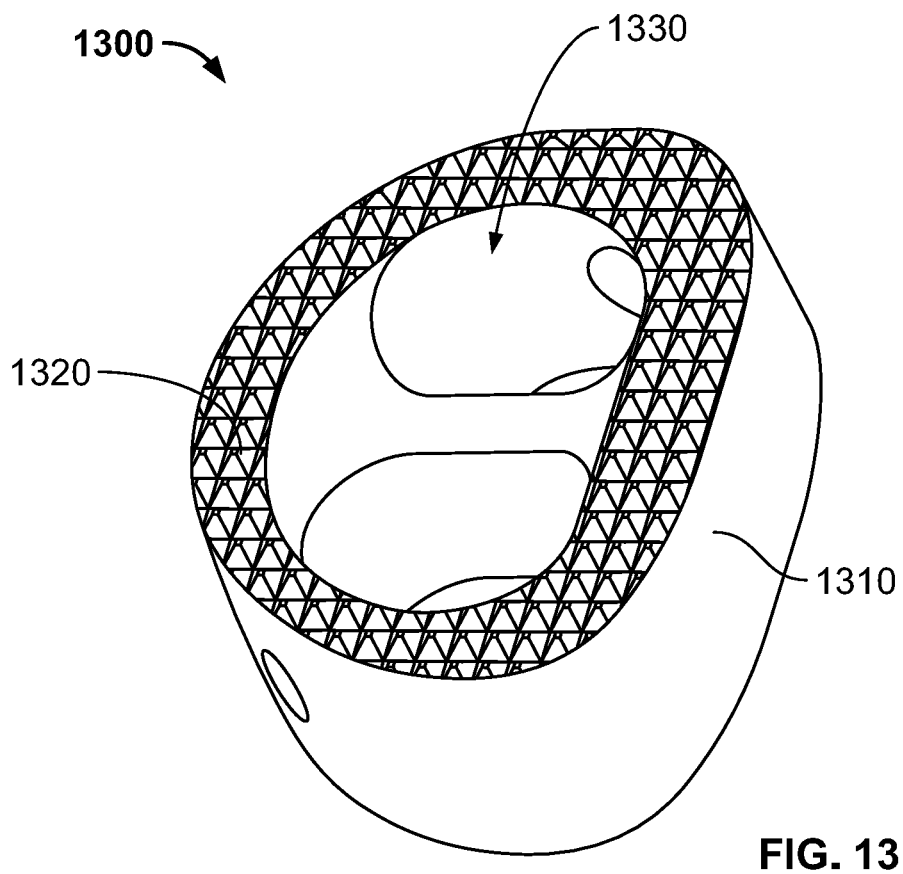
Figure 14:
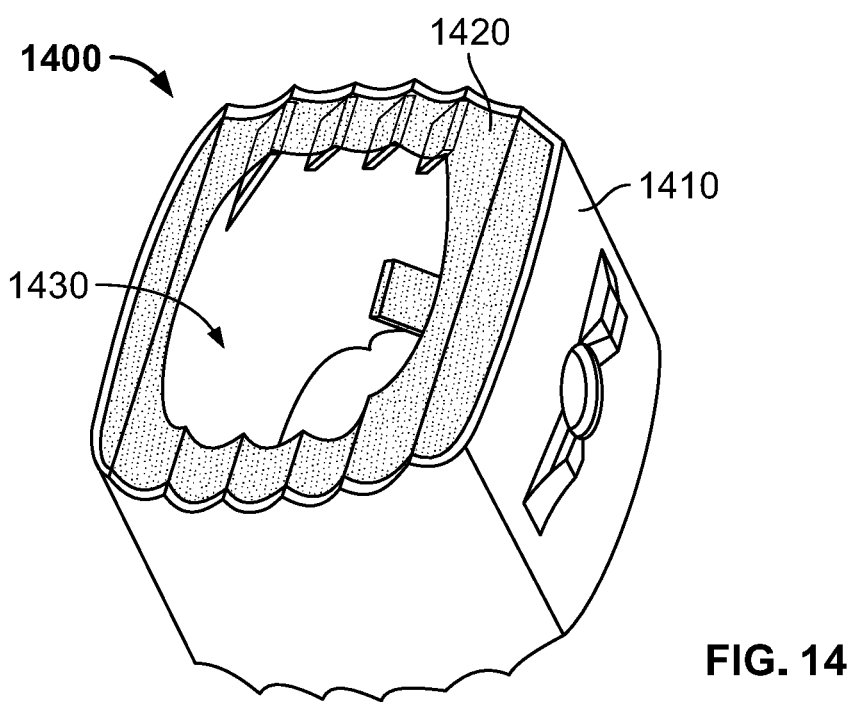
Figure 15:
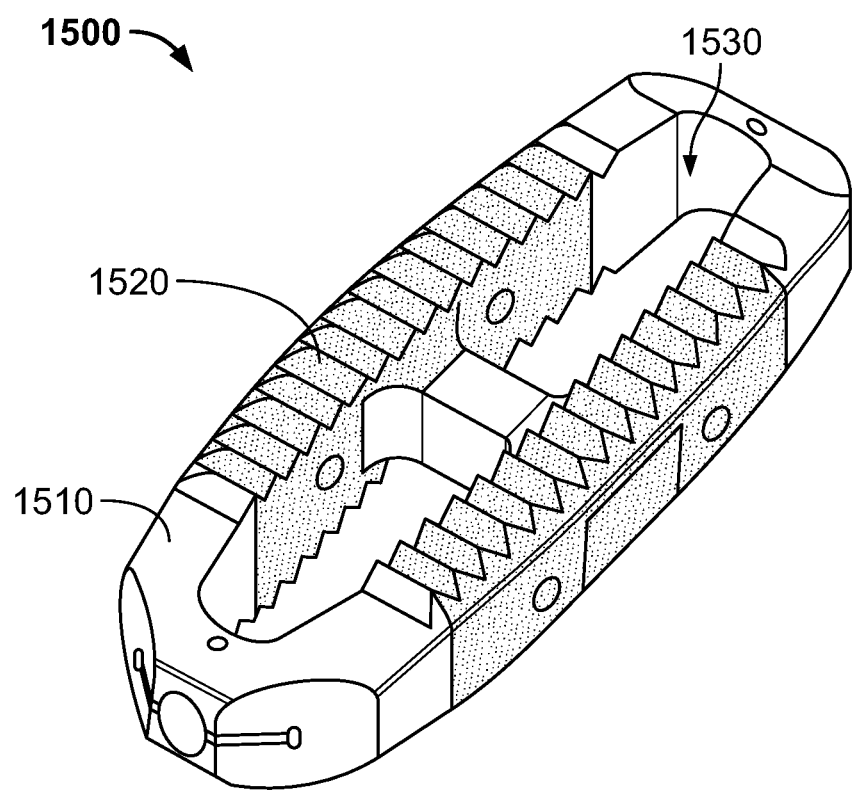

FIGS. 11A and 11B depict an even further embodiment IBD 1100, which is particularly suited for implantation into a lumbar disc space via a posterior approach. IBD 1100 generally includes a solid outer wall 1110 and a porous body or core 1120. Outer wall 1110 surrounds porous core and forms a nose at a leading end 1103. Outer wall 1110 helps provide strength to device 1100 particular for insertion. However, to reduce the stiffness of IBD 1100, a lateral window 1132 extends laterally through IBD 1100 including through outer wall 1110 and porous core 1120. Also, a threaded opening 1114 extends into a trailing end 1101 of IBD 1100 for connection to an inserter instrument (not shown). Moreover, unlike IBD 1000, IBD 1100 includes a graft window 1130 extending from a superior side to an inferior side thereof and intersects lateral graft window 1132. Serrations or teeth 1112 extend inwardly from solid outer wall 1110 and are embedded in porous structure 1120, such that teeth 1112 sit proud of porous core 1120 for direct engagement with bone.

Porous core 11120 includes a porous structure similar to that of IBD 1000 in that porous core 1120, in addition to having a plurality of pores defined by cells thereof, includes tissue through-channels 1124 extending from a superior side to an inferior side thereof. Also, tissue-channels 1124 optionally include elongate struts 1126 lining each of through-channels 1124 for support of the porous structure 1122 adjacent channels 1124. As shown in FIG. 11A, at least one through-channel 1124 is situated between each serration. Also, through-channels 1124 are interrupted by lateral window 1132, and are substantially smaller in cross-sectional dimension than graft window 1130. This is at least because graft window 1130 is intended to be packed with a bone graft material, while through-channels 1124 may either remain empty to facilitate tissue cell transfer or may be filled with a bioactive material. However, it is preferable that through-channels 1124 remain free from obstruction. Thus, in embodiments where porous core 1120 is impregnated with a bioactive material, as discussed above, through channels 1124 may be plugged during an injection molding process and later unplugged so that, while the porous structure 1122 of porous core 1124 may have bioactive material dispersed therein, tissue-channels 1124 remain clear of the same.

FIGS. 12-15 depict additional IBD embodiments that can deploy one or more of the optimization features described herein. Such IBD's include IBD 1300 which is particular configured for implantation into a disc space via a posterior approach, IBD 1400 which is particularly configured for a posterolateral approach, IBD's 1500 and 1600 which are particularly configured for an anterior approach, and IBD 1700 which is particularly configured for a lateral approach. More particularly, IBD's 1200, 1300, 1400, and 1500 similarly include solid reinforcing structures 1210, 1310, 1410, and 1510, porous structures 1220, 1320, 1420, and 1520, and graft windows 1230, 1330, 1430, and 1530 such that they can be modified to include any one or more of the optimization features described herein. These IBD's and additional IBD's that can be modified to incorporate any of the previously described features is discussed in more detail in U.S. Pub. No. 2016/0199193, which is hereby incorporated by reference in its entirety herein. In this regard, each of these IBD's can have one or more of a strain optimized porous structure, a porous structure with varying porosities, a porous structure and/or graft window impregnated with a bioactive material, and tissue-through channels extending from one bone interface to another bone interface, for example. Moreover, any one of IBD's 1200, 1300, 1400, and 1500, while depicting graft windows, may be windowless and instead include porous material located in the spaces of windows 1230, 1330, 1430, and 1530 so that such porous material can have varying porosities for facilitating bone ingrowth, as described herein.

Also, any of the IBD's disclosed herein, such as IBD's 300, 400, 500, 600, 700, 800, 900, 1000, and 1100 can include one or more of the optimization features described herein. For example, all of these IBD's have porous structures which can be manufactured to have varying porosities to achieve desired objectives, such as mimicking bone densities, encouraging both initial and long term connection strength, and resisting subsidence. Also, the porous structures of these IBD's may be impregnated with a bioactive material and/or may be strain optimized to have strains during operation that fall within a predetermined strain range conducive to bone growth. In addition, IBD's 300, 400, 500, 600, 700, 800, and 900 may further include tissue through-channels. In this regard, such through-channels may extend between every other bone engaging projection of IBD's 400 and 500, and may align with the through-channels of outer layer of IBD 600, for example. Moreover, with regard to IBD 700, tissue through-channels may extend from superior to inferior surfaces thereof so that such channels extend through more than one, but less than all, of the openings defined in gridded reinforcement members.

Also, while the above described implant modifications are exemplified by spinal implants, such implant optimization modifications can be used in any orthopedic application, particularly those where bone ingrowth is desirable. One such orthopedic application includes filling bone voids in knee revision procedures using bone void filling prostheses, such as those described in U.S. Pat. No. 9,668,758, which is hereby incorporated by reference herein in its entirety. Such void filling prostheses have a porous structure that can include some or all of the optimization features disclosed herein. For instance, the porous structure of a void filling prosthesis may have a varying porosity such that successive layers thereof have differing porosities, be impregnated with bioactive glass, and/or be strain optimized, as described above. In another example, hip or knee implants and the like may include any one of the above described features. More particularly, an intramedullary stem of an endoprosthesis may have any one of or all of a varying porosity, tissue through-channels, a porous structure impregnated with a bioactive material, and a strain optimized porous structure. Even further, the porous interfaces between a tibial baseplate and resected tibia, femoral component and resected distal femur, acetabular cup and resected acetabulum, and the like may include any one of the above described features to help promote bone ingrowth and minimize stress shielding.

The exemplary implants described herein and the features thereof may be formed layer-by-layer using an additive layer manufacturing (ALM), i.e., 3D printing, process so no separate connection mechanism is necessary to bring together any of the components of such implants. In some examples, ALM processes are powder-bed based and involve one or more of selective laser sintering (SLS), selective laser melting (SLM), and electron beam melting (EBM), as disclosed in the heretofore referenced '901 Patent as well as U.S. Pat. Nos. 7,537,664; 8,728,387; 9,180,010 and U.S. Patent Publication No. 2006/0147332, each of which is hereby incorporated by reference in their entireties herein. Other methods of ALM, which can be used to form the herein described implants, include stereolithography (SLA), fused deposition modeling (FDM), and continuous liquid interface production (CLIP).

When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the solid and porous layers and any other components, as applicable. In some instances, materials for one layer may be different than the materials for successive layers. This process allows for porous portions to extend full thickness through a particular structure, such as the porous cores of the IBD's described above. It also allows porous portions to be formed in locations impossible to reach by other methods, such as adjacent through-channels 1022 and 1122 and in connection with struts 1026 and 1126 of implants 1000 and 1100, respectively. Moreover, it allows intricate structures to be formed, such as cell 100 and lattice structure 150 formed thereof, where traditional forms of subtractive manufacturing fall short.

Each of solid and porous layers of the above described implants may be constructed from biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium, or biocompatible polymers, such as but not limited to any one of or any combination of polyethylene (PE) and variations thereof, polyetheretherketone (PEEK), polyetherketone (PEK), acrylonitrile butadiene styrene (ABS), silicone, and cross-linked polymers. In some arrangements, the implants described herein may be made of certain other materials such as but not limited to bioabsorbable glass, ceramics, and biological active materials including collagen/cell matrices. In some arrangements, the implant may be made of a combination of any of these metals, polymers, and other materials. All constituent porous and solid portions of the above described implants may be a common material, such as one of those listed above, or different materials can be employed for each part. Particular combinations of materials and their use for specific parts of herein described implants are a matter of design choice and may include the combination of different metals, different polymers, or metals combined with polymers. For example, the solid portions of the herein described implants can be made from a metal while the porous portions may be made from a polymer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal interbody device (IBD) comprising:
a solid wall at least partially defining a boundary of the IBD; and
a porous body connected to the solid wall and having a plurality of sections forming at least a portion of both a superior and inferior bone interface side of the IBD, wherein each section of the porous body has a different porosity than an adjacent section such that the porosities increase toward a center of the IBD.

2. The IBD of claim 1, wherein the plurality of sections include first and second sections, the first section forming a ring about the second section.

3. The IBD of claim 2, wherein at least the first section is impregnated with a bioactive material so that particles of the bioactive material are disposed within pores of the porous first section.

4. The IBD of claim 3, wherein a pore size of the second section is smaller than a particle size of the bioactive material such that the second section is substantially free from the bioactive material.

5. The IBD of claim 1, further comprising solid projections embedded in the porous body and extending from the superior and inferior bone interface sides of the IBD.

6. The IBD of claim 1, further comprising a plurality of elongate through-channels extending entirety through the porous body from the superior bone interface side to the inferior bone interface side of the IBD.

7. The IBD of claim 6, further comprising a plurality elongate struts each partially defining a perimeter of a respective one of the elongate through-channels.

8. The IBD of claim 1, wherein the porous body comprises a plurality of adjoined cells that collectively define a plurality of pores of the porous body, each cell of the porous body having a plurality of connected members.

9. The IBD of claim 8, wherein the members of each cell have a different cross-sectional dimension based on their expected loads such that they each have a strain of between 1000 and 1800 micro strain when implanted in a disc space.

10. The IBD of claim 8, wherein the cells of the porous body each have a geometric shape selected from the group consisting of a diamond cubic, single cubic, body-centered cubic, face centered cubic, tetrahedron, dodecahedron, or octahedron.

11. The IBD of claim 8, wherein each section of the porous body includes cells of a different geometric shape than an adjacent section.

12. The IBD of claim 1, wherein the porous body completely fills a space confined by the solid wall.

13. The IBD of claim 1, wherein the solid wall includes bone engaging projections extending from superior and inferior sides thereof.

14. A spinal interbody device (IBD) comprising:
a solid wall; and
a porous body positioned within a boundary defined by the solid wall, the porous body having a plurality of sections such that a first section of the plurality of sections forms an outer bone contacting layer of the porous body and a second section of the plurality of sections forms an inner layer of the porous body so that when the IBD is implanted within a disc space defined partially by a vertebra, the first section is positioned closer to the vertebra than the second section, the first section having a first porosity that differs from a porosity of the second section.

15. The IBD of claim 14, wherein the first section has a smaller porosity than the second section.

16. The IBD of claim 14, wherein the first section has a greater porosity than the second section.

17. The IBD of claim 16, wherein at least the first section is impregnated with a bioactive material so that particles of the bioactive material are disposed within pores of the porous first section.

18. The IBD of claim 17, wherein a pore size of the second section is smaller than a particle size of the bioactive material such that the second section is substantially free from the bioactive material.

19. The IBD of claim 14, further comprising solid projections embedded in the first section of the porous body and extending therefrom.

20. The IBD of claim 14, further comprising a plurality of elongate through-channels extending entirely through the porous body from a superior side to an inferior side of the IBD and a plurality of elongate struts each partially defining a perimeter of a respective one of the elongate through-channels.

\* \* \* \* \*